United States Patent
Winzenberg et al.

(10) Patent No.: US 7,705,038 B2
(45) Date of Patent: Apr. 27, 2010

(54) CONTROL OF PARASITES IN ANIMALS BY THE USE OF PARASITICIDAL 2-PHENYL-3-(1H-PYRROL-2-YL)ACRYLONITRILE DERIVATIVES

(75) Inventors: Kevin N. Winzenberg, Camberwell (AU); Simon Saubern, East St. Kilda (AU); David G. Sawutz, Maplewood, NJ (US)

(73) Assignee: Intervet, Inc., Roseland, NJ (US)

(*) Notice: Subject to any disclaimer, the term of this patent is extended or adjusted under 35 U.S.C. 154(b) by 621 days.

(21) Appl. No.: 11/280,739

(22) Filed: Nov. 16, 2005

(65) Prior Publication Data

US 2006/0128779 A1 Jun. 15, 2006

Related U.S. Application Data

(60) Provisional application No. 60/629,699, filed on Nov. 19, 2004.

(51) Int. Cl.
*A61K 31/40* (2006.01)
(52) U.S. Cl. .................................................. 514/427
(58) Field of Classification Search .................. 514/427
See application file for complete search history.

(56) References Cited

U.S. PATENT DOCUMENTS

| | | |
|---|---|---|
| 3,370,063 A | 2/1968 | Suh |
| 3,381,006 A | 4/1968 | Suh et al. |
| 3,454,586 A | 7/1969 | Suh |
| 3,467,670 A | 9/1969 | Suh |
| 3,491,114 A | 1/1970 | Suh |
| 3,852,416 A | 12/1974 | Grubb, et al. |
| 3,950,360 A | 4/1976 | Aoki et al. |
| 3,984,564 A | 10/1976 | Aoki et al. |
| 4,199,569 A | 4/1980 | Chabala et al. |
| 4,224,901 A | 9/1980 | Carey, Jr. |
| 4,310,519 A | 1/1982 | Albers-Schonberg et al. |
| 4,311,857 A | 1/1982 | Nagabhushan |
| 4,582,918 A | 4/1986 | Nagabhushan et al. |
| 4,743,700 A | 5/1988 | Jommi et al. |
| 4,820,695 A | 4/1989 | Debono et al. |
| 4,876,352 A | 10/1989 | Schumacher et al. |
| 4,916,154 A | 4/1990 | Asato et al. |
| 4,973,750 A | 11/1990 | Nagabhushan et al. |
| 5,089,480 A | 2/1992 | Gibson et al. |
| 5,105,009 A | 4/1992 | Jommi et al. |
| 5,184,573 A | 2/1993 | Stevens, Jr. |
| 5,227,494 A | 7/1993 | Schumacher et al. |
| 5,288,710 A | 2/1994 | Cvetovich |
| 5,352,832 A | 10/1994 | Wu et al. |
| 5,382,673 A | 1/1995 | Clark et al. |
| 5,399,717 A | 3/1995 | Cvetovich et al. |
| 5,555,848 A | 9/1996 | Trujillo et al. |
| 5,567,844 A | 10/1996 | Jommi et al. |
| 5,663,361 A | 9/1997 | Towson et al. |
| 5,958,888 A | 9/1999 | Macy et al. |
| 6,054,434 A | 4/2000 | Kropp et al. |
| 6,239,112 B1 | 5/2001 | Macy et al. |
| 6,270,768 B1 | 8/2001 | O'Connell et al. |
| 6,271,255 B1 | 8/2001 | Leadlay et al. |
| 6,339,063 B1 | 1/2002 | Kropp et al. |
| 6,437,151 B2 | 8/2002 | Leadlay et al. |
| 6,472,371 B1 | 10/2002 | Dirlam et al. |
| 6,514,945 B1 | 2/2003 | Boettner |
| 2003/0064939 A1 | 4/2003 | Sklavounos et al. |
| 2004/0082553 A1 | 4/2004 | Boojamra et al. |
| 2005/0182031 A1 | 8/2005 | Hecker et al. |
| 2005/0182059 A1 | 8/2005 | Winzenberg et al. |
| 2005/0182139 A1 | 8/2005 | Shuster et al. |
| 2006/0063841 A1 | 3/2006 | Meyer et al. |
| 2006/0281695 A1 | 12/2006 | Meyer et al. |

FOREIGN PATENT DOCUMENTS

| | | |
|---|---|---|
| EP | 0 557 732 A1 | 9/1993 |
| EP | 1088811 | 11/2002 |
| JP | 61090165 | 5/1986 |
| JP | 5100264 | 4/1993 |
| WO | WO 98/35935 A | 8/1998 |

OTHER PUBLICATIONS

Vippagunta, et al. Advanced Drug Delivery Reviews 48 (2001) 3-26.*
International Search Report, International Application No. PCT/US2005/041374, Date of Mailing: May 12, 2006.
Abstract, Alberghina, et al., Journal of Heterocyclic Chemistry, "Proton NMR, ultraviolet, and infrared spectra of some (Z)-.alpha.-(phenyl)-.beta.-(2-furyl),-(2-pyrroly), and-(N-methyl-2-pyrrolyl)acrylonitriles", 23 (6), 1986, pp. 1747-1752.
Abell, et al., Australian Journal of Chemistry, "Synthesis and amino acid chain extension of 1-acylated hydroxymethylpyrroles", vol. 46, No. 10, 1993, pp. 1473-1483 (Abstract Only).
Bergauer, et al., Synthesis, "Diethoxymethyl Protected Pyrroles: Synthesis and Regioselective Transformations", No. 15, 2001, pp. 2281-2288.
Caccamese, et al., J. of Liquid Chromatography & Related Technologies, "Substituent Effects in High-Performance Liquid Chromatography of Diarylacrylonitriles", vol. 7, No. 13, 1984, pp. 2631-2642 (Abstract Only).

(Continued)

*Primary Examiner*—Rebecca L Anderson
*Assistant Examiner*—Shawquia Young
(74) *Attorney, Agent, or Firm*—David J. Kerwick

(57) ABSTRACT

2-Phenyl-3-(1H-pyrrol-2-yl)acrylonitrile compounds useful for controlling parasites in animals and methods of treatment of parasite infestation in animals using the compounds are disclosed.

23 Claims, 1 Drawing Sheet

OTHER PUBLICATIONS

Castells, et al., Tetrahedron, "Synthesis and Reactivity of 2-(1,3-Dithian-2-yl)Indoles, IV. Influence of the N, N-Diethylcarbamoyl Indole Protecting Group", vol. 47, No. 37, 1991, pp. 7911-7924.

Grehn, et al., Angew. Chem. Int. Ed. Engl., "A Convenient Method for the Preparation of 1-(tert-Butyloxycarbonyl)pyrroles", vol. 23, No. 4, 1984, pp. 296 & 301.

Herz, et al., J. Org. Chem., "Pyrroles. XII. The Reaction of Pyrroleaidehydes with Arylacetonitriles", vol. 23, 1958, pp. 711-714.

Jaureguiberry, et al., Comptes Rendus des Seances de l'Academie des Scienses, Serie C: Sciences Chimiques, "Bromination of alpha-formylpyrroles in the presence of excess aluminum chloride", vol. 273, No. 3, 1971, pp. 276-277 (Abstract Only).

Pesson, et al., Compt. Rend., "Alkylation of phenylacetonitrile by 1-ethyl-3-chloropiperidine", vol. 259, No. 25, 1964, pp. 4716-4718 (Abstract Only).

Robinson, et al., Tetrahedron, "Replacement Substituent Constants for Simple Heterocycles", vol. 45, No. 13, 1989, pp. 4103-4112.

Sonnet, The Journal of Organic Chemistry, "Preparation and Properties of Ternary Iminium Salts of Pyrrole Aldehydes and Ketones. Synthesis of 4-Substituted Pyrrole-2-carboxaldehydes", vol. 37, No. 7, 1972, pp. 925-929.

Tietze, et al., Liebigs Annalen der Chemie, "Intra- and intermolecular hetero-Diels-Alder reactions. XIX.Stereoselective synthesis of five- and seven-membered annulated ring systems by intramolecular hetero-Diels-Alder reaction", vol. 1, 1988, pp. 9-12 (Abstact Only).

Watanabe, et al., Chemical & Pharmaceutical Bulletin, "Synthetic studies on indoles and related compounds, XXVI. The debenzylation of protected indole nitrogen with aluminum chloride", vol. 39, No. 5, 1991, pp. 1152-1156 (Abstract Only).

Wolff, et al., J. Org. Chem, "C-19 Functional Steroids. X. 17beta-Hydroxy-1beta,19-cyclo-5alpha-androstan-2-one and Related Compounds", vol. 30, 1965, pp. 2553-2557.

* cited by examiner (Scheme 1)

CONTROL OF PARASITES IN ANIMALS BY THE USE OF PARASITICIDAL 2-PHENYL-3-(1H-PYRROL-2-YL)ACRYLONITRILE DERIVATIVES

CROSS-REFERENCE TO RELATED APPLICATIONS

This application is a non-provisional application that claims priority under 35 U.S.C. §119(e) of provisional application U.S. Ser. No. 60/629,699 filed Nov. 19, 2004, the contents of which are hereby incorporated by reference in their entireties.

FIELD OF THE INVENTION

The present invention relates to methods of killing, suppressing and/or treating ecto- and endoparasite infections or infestations using 2-phenyl-3-(1H-pyrrol-2-yl)acrylonitrile compounds and compositions containing these compounds, both in vivo and ex vivo, and in the general environment, by the application or administration of these compounds.

BACKGROUND OF THE INVENTION

The control of animal parasites is essential, especially in the areas of food production and companion animals. Existing methods of treatment and parasite control are being compromised due to growing resistance to current commercial parasiticides, such as the benzimidazoles and ivermectins. The discovery of more effective ways to control animal parasites is therefore imperative.

The literature has reported several derivatives of the 2-phenyl-3-(1H-pyrrol-2-yl)acrylonitrile ring system, that are based on Formula 1,

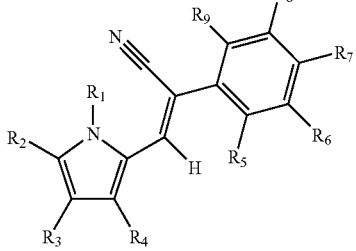

Formula 1 wherein $R_1$ is not aryl or heteroaryl. These include 3-(2-pyrrolyl)-2-(4,5-dimethoxy-2-nitrophenyl)acrylonitrile and 3-(1-methyl-2-pyrrolyl)-2-(4,5-dimethoxy-2-nitrophenyl) acrylonitrile, described in *J. Org. Chem.*, 30, 1965, 2553;

3-(2-pyrrolyl)-2-(4-substitutedphenyl)acrylonitrile and 3-(1-methyl-2-pyrrolyl)-2-(4-substitutedphenyl)acrylonitrile derivatives. The para substituent is H, Me, MeO, Cl and $NO_2$, described in *J. Heterocyclic Chem.*, 23, 1986, 1747; 3-(2-pyrrolyl)-2-(4-substitutedphenyl)acrylonitrile and 3-(1-methyl-2-pyrroly)-2-(4-substitutedphenyl)acrylonitrile derivatives. The para substituent is H, Me, MeO, Cl and $NO_2$, described in *J. Liquid Chromatography*, 7, 1984, 2631; 3-(2-pyrrolyl)-2-(phenyl)acrylonitrile, described in *Tetrahedron*, 45, 1989. 3-(2-pyrrolyl)-2-(4-substitutedphenyl)acrylonitrile and 3-(1-methyl-2-pyrrolyl)-2-(4-substitutedphenyl)acrylonitrile derivatives. The para substituent is H, Me, MeO, Cl and $NO_2$, as described in *Journal of Organic Chemistry*, 1958, 23, 711-14;

Some general synthetic routes to compounds of this type, such as 3-(2-pyrrolyl)-2-(phenyl)acrylonitrile, have been described (see, *Journal of Organic Chemistry*, 1958, 23, 711-14, cited above).

However, previously reported methods of using compounds of this type are limited to cough suppression and the materials sciences, e.g., as light absorbing agents, including, 3-(2-pyrrolyl)-2-(4,5-dimethoxy-2-nitrophenyl)acrylonitrile, and 3-(1-methyl-2-pyrrolyl)-2-(4,5-dimethoxy-2-nitrophenyl) acrylonitrile, as described by U.S. Pat. Nos. 3,370,063, 3,381, 006, 3,454,586, 3,467,670 and 3,491,114, and as photosensitive dyes, as described by JP5100264 and JP6190165. JP 6190165 describes 3-(2-pyrrolyl)-2-phenylacrylonitrile derivatives that contain nitro and/or amino substituent at the para position of the phenyl ring and the 5 position of the pyrrole. In particular, cough suppression is the only biological activity reported for phenyl pyrrole acrylonitriles of Formula 1, wherein R1 is not aryl or heteroaryl [*Compt. Rend.*, 259, 1964, 4716-18, describing 3-(1-ethyl-2-pyrrolyl)-2-(phenyl)acrylonitrile].

The citation of any reference herein should not be construed as an admission that such reference is available as "prior art" to the instant application.

SUMMARY OF THE INVENTION

Accordingly, the present invention provides methods of treating, preventing, inhibiting and/or killing ecto and/or endoparasites using one or more of the 2-phenyl-3-(1H-pyrrol-2-yl)acrylonitrile compounds identified herein that are effective anti-parasite agents.

Therefore, the invention provides methods of treating, preventing (including as metaphylaxis), killing, inhibiting, and/or suppressing the growth of an ecto- and/or endoparasite. One such method comprises contacting the susceptible ecto- and/or endoparasite with an effective amount of an anti-parasite agent of the present invention. In a particular embodiment of this type, the effective anti-parasite agent is administered to and/or on an animal being treated that has the ecto- and/or endoparasite. In another embodiment, an effective anti-parasite agent is administered to the environment (e.g., a stall or blanket) in which an animal resides. In still another embodiment, the effective anti-parasite agent is administered to a plant and/or foliage.

In a particular embodiment, the invention provides a method of treating, preventing (including as metaphylaxis), killing, inhibiting, and/or suppressing the growth of an ecto- or endoparasite, that comprises contacting a susceptible ecto- or endoparasite with an effective amount of a 2-phenyl-3-(1H-pyrrol-2-yl)acrylonitrile compound of Formula 1:

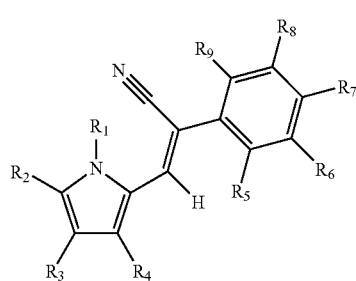

Formula 1 or a pharmaceutically acceptable salt thereof, or a solvate thereof.

In Formula 1, $R_1$ is selected from the group consisting of H, lower alkyl, and one of the following optionally substituted groups, alkoxyalkyl, alkoxyalkoxyalkyl, 1,1-(dialkoxy)alkyl, 1-alkoxy-1-alkylmethyl, aroyl, alkanoyl, arylalkyl, alkyloxyalkanoyl, alkoxycarbonyl, arylalkoxycarbonyl, arylsulfonyl, alkylarylsulfonyl, alkylalkenyl, N-alkylcarbamoyl, N,N-dialkylcarbamoyl, N-alkylthiocarbamoyl, N,N-dialkylthiocarbamoyl; and wherein, $R_2$-$R_9$ are independently selected from the group consisting of H, nitro, cyano, halo, and one of the following optionally substituted groups, alkyl, aryl, cycloalkyl, cycloalkenyl, alkylcycloalkyl, alkylcycloalkenyl, cycloalkylalkyl, arylalkyl, aryloxyalkyl, arylthioalkyl, haloalkyl, haloalkenyl, haloalkynyl, haloaryl, halocycloalkyl, alkoxy, alkenyloxy, alkynyloxy, aryloxy, cycloalkyloxy, cycloalkenyloxy, alkylcycloalkyloxy, alkylcycloalkenyloxy, cycloalkylalkyloxy, arylalkoxy, aryloxyalkoxy, arylthioalkyloxy, haloalkoxy, haloalkenyloxy, haloalkynyloxy, haloaryloxy and halocycloalkoxy.

Another embodiment of the invention provides a method of killing, or suppressing the growth of an ecto- or endoparasite, comprising contacting a susceptible ecto- or endoparasite with an effective amount of a 2-phenyl-3-(1H-pyrrol-2-yl)acrylonitrile compound of Formula 1, wherein, $R_1$ is selected from the group consisting of H, and one of the following optionally substituted groups, lower alkyl, alkoxyalkyl, alkoxyalkoxyalkyl, 1,1-(dialkoxy)alkyl, 1-alkoxy-1-alkylmethyl, aroyl, alkanoyl, arylalkyl, alkoxycarbonyl, arylalkoxycarbonyl, arylsulfonyl, alkylarylsulfonyl, alkylalkenyl, N-alkylcarbamoyl, N,N-dialkylcarbamoyl, N-alkylthiocarbamoyl and N, N-dialkylthiocarbamoyl, and wherein, $R_2$-$R_9$ are independently selected from the group consisting of H, nitro, cyano, halo, and one of the following optionally substituted groups, alkyl, alkenyl, alkynyl, aryl, cycloalkyl, haloalkyl, haloalkenyl, haloalkynyl, haloaryl, halocycloalkyl, alkoxy, alkenyloxy, aryloxy, cycloalkyloxy, arylalkoxy, aryloxyalkoxy, haloalkoxy, haloalkenyloxy, haloaryloxy, alkylthio, arylthio, cycloalkylthio, arylalkylthio, aryloxyalkylthio, or a pharmaceutically acceptable salt thereof or a solvate thereof.

In yet another embodiment, the invention provides a method of killing, or suppressing the growth of an ecto- or endoparasite, comprising contacting a susceptible ecto- or endoparasite with an effective amount of a 2-phenyl-3-(1H-pyrrol-2-yl)acrylonitrile compound of Formula 1 wherein, $R_2$-$R_4$ are independently selected from H, halo, optionally substituted alkyl or alkoxy, or a pharmaceutically acceptable salt or solvate thereof, and wherein, $R_5$-$R_9$ are independently selected from the group consisting of H, nitro, cyano, halo, and one of the following optionally substituted groups, alkyl, alkenyl, alkynyl, aryl, cycloalkyl, haloalkyl, haloaryl, halocycloalkyl, alkoxy, alkenyloxy, aryloxy, cycloalkyloxy, arylalkoxy, haloalkoxy and haloaryloxy. Optionally, $R_5$ and $R_6$ or $R_6$ and $R_7$ are combined or connected to provide a fused ring consisting of 5-7 members, or a pharmaceutically acceptable salt thereof or a solvate thereof.

In a preferred embodiment, the inventive method is conducted with a compound of Formula 1 wherein, $R_1$ is selected from the group consisting of H, $CH_3$, ethoxymethyl ["EOM"], diethoxymethy ["DOM"], propanoyl, benzyl, $(CH_3CH_2)_2NC(O)$ ["$Et_2NC(O)$"], tert-butoxycarbonyl ["Boc"], 2-methyl prop-1-enyl, benzoyl, p-toluenesulfonate ("tosyl"), $(CH_3)_2NC(O)$ ["$Me_2NC(S)$"], $CH_3OC(O)$ ["MeOC(O)"] and benzyloxycarbonyl ["Cbz"];

$R_2$ is H or Cl;
$R_3$ is selected from the group consisting of H, Cl or Br;
$R_4$ is always H;
$R_5$ is selected from the group consisting of H, Cl, Br $CH_3$, nitrile, $CF_3$, phenyl and $OCH_3$ ["OMe" or "methoxy"];
$R_6$ is selected from the group consisting of H, Cl, F, Br, $CF_3$, O-phenyl and $CH_3$;
$R_7$ is selected from the group consisting of H, Cl, F, $CH_3$, methoxy, t-butyl, phenyl, and nitrile; and $R_8$ and $R_9$ are independently, H, halo or $CF_3$. Optionally, in certain embodiments, $R_5$ and $R_6$ or $R_6$ and $R_7$ are aryl, and are linked by a —CH═CH—CH═CH— moiety, so that $R_5$ and $R_6$ or $R_6$ and $R_7$ form a naphthyl moiety.

More preferably, the inventive method is conducted with a 2-phenyl-3-(1H-pyrrol-2-yl)acrylonitrile compound of Formula 1 is selected from the group identified in Tables 1a and 1b, or a pharmaceutically acceptable salt thereof or a solvate thereof.

Preferably, the parasite to be killed or suppressed is an ectoparasite or an endoparasite, that can be present in the environment, on or within a plant or animal (ex vivo or in vivo).

In an optional embodiment, the inventive method is conducted with one or more 2-phenyl-3-(1H-pyrrol-2-yl)acrylonitrile compounds in combination with, simultaneously or sequentially, any other art-known for killing or controlling various types of pests.

In certain particular embodiments, the invention also provides for new 2-phenyl-3-(1H-pyrrol-2-yl)acrylonitrile compounds of Formula 1, that are one or more of compounds 10, 15, 16, 25 and 28 of Tables 1a and 1b and/or a pharmaceutical composition that includes a therapeutically effective dosage amount thereof, and a pharmaceutically acceptable excipient.

The invention also provides for new 2-phenyl-3-(1H-pyrrol-2-yl)acrylonitrile compounds of Formula 1, that are one or more of compounds 77-80 and 82 of Table 1a and/or a pharmaceutical composition that includes a therapeutically effective dosage amount of thereof, and a pharmaceutically acceptable excipient.

DETAILED DESCRIPTION OF THE INVENTION

Figure 1:
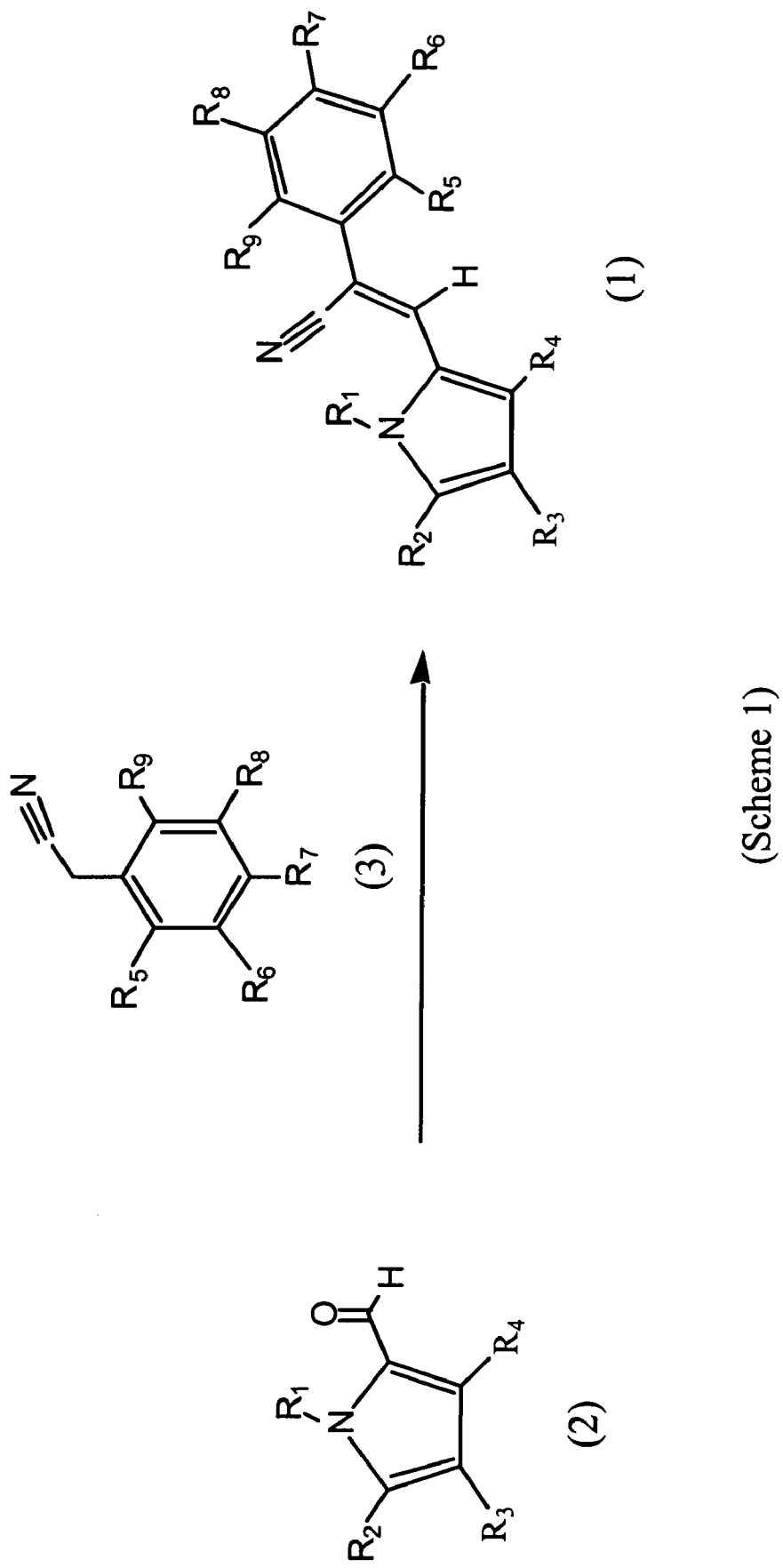
FIG. 1 illustrates reaction Scheme 1, wherein a 1H-pyrrole-2-carbaldehyde derivative of Formula 2 is reacted with a phenylacetonitrile derivative of Formula 3 to provide a compound of Formula 1.

The present invention provides methods of treating and/or preventing (including metaphylaxis) ecto- and/or endoparasite infestations of animals, as well as methods of killing, inhibiting and/or suppressing the growth of such parasites by contacting such parasites with the 2-phenyl-3-(1H-pyrrol-2-yl)acrylonitrile derivatives described herein.

In order to more fully appreciate the description of the invention, the following terms are employed as defined below, unless otherwise indicated.

The use of singular terms for convenience in description is in no way intended to be so limiting. Thus, for example, reference to "a parasite" includes reference to one or more of such parasites. The use of plural terms in also not intended to be limiting, unless otherwise specified. For example, the phrase, "2-phenyl-3-(1H-pyrrol-2-yl)acrylonitrile compounds" refers to one or more of the 2-phenyl-3-(1H-pyrrol-2-yl)acrylonitrile compound identified herein, and includes a single such compound alone, or a combination of two or more such compounds.

As used herein the term "approximately" is used interchangeably with the term "about" and generally signifies that a value is within twenty percent of the indicated value, unless otherwise indicated.

In this specification "optionally substituted" means that a functional group is either substituted or unsubstituted, at any available position. Substitution can be with one or more functional groups selected from, e.g., alkyl, alkenyl, alkynyl, aryl, cycloalkyl, cycloalkenyl, alkylcycloalkyl, alkylcycloalkenyl, arylcycloalkyl, arylcycloalkenyl, halo, cyano, nitro, haloalkyl, haloalkenyl, haloalkynyl, haloaryl, halocycloalkyl, halocycloalkenyl, hydroxy, alkoxy, cycloalkoxy, alkenyloxy, aryloxy, haloalkoxy, haloalkenyloxy, haloaryloxy, halocycloalkyloxy, heterocyclyl, heterocyclyloxy, heterocyclylamino, heterocyclylalkyl, heterocyclyloxyalkyl, heterocyclylthioalkyl, haloheterocyclyl, haloheterocyclylalkyl, haloheterocyclyloxyalkyl, haloheterocyclylthioalkyl, nitroaryl, nitroheterocyclyl, amino, akylamino, dialklamino, alkenylamino, alkynylamino, arylamino, acyl, alkenylacyl, arylacyl, acylamino, alkylsulphonyloxy, alkoxycarbonyl, alkylthio, alkylsulphonyl, arylthio, arylsulphonyl, aminosulphonyl, dialkylaminosulphonyl, and any other art-known substituents.

"Alkyl," whether used alone, or in compound words such as alkoxyalkyl, alkoxyalkoxyalkyl, alkoxy, alkylthio, alkylamino, dialkylamino or haloalkyl, represents straight or branched chain hydrocarbons ranging in size from one to about 20 carbon atoms, or more. Thus, alkyl moieties include, without limitation, those ranging in size, for example, from one to about 10 carbon atoms or greater, e.g., methyl, ethyl, n-propyl, iso-propyl and/or butyl, pentyl, hexyl, and higher isomers, including, e.g., those straight or branched chain hydrocarbons ranging in size from about 11 to about 20 carbon atoms, or greater. Preferably, a "Lower alkyl" means a group having 1 to about 6 carbons in the chain, which may be straight or branched.

"Alkenyl," whether used alone, or in compound words such as alkenyloxy or haloalkenyl, represents straight or branched chain hydrocarbons containing at least one carbon-carbon double bond, including, without limitation, moieties ranging in size from two to about 6 carbon atoms or greater, such as, methylene, ethylene, 1-propenyl, 2-propenyl, and/or butenyl, pentenyl, hexenyl, and higher isomers, including, e.g., those straight or branched chain hydrocarbons ranging in size, for example, from about 2 to about 20 carbon atoms, or greater. Preferably, an alkenyl ranges in size from 2 to about 6 carbons.

"Alkynyl," whether used alone, or in compound words such as alkynyloxy, represents straight or branched chain hydrocarbons containing at least one carbon-carbon triple bond, including, without limitation, moieties ranging in size from, e.g., two to about 6 carbon atoms or greater, such as, ethynyl, 1-propynyl, 2-propynyl, and/or butynyl, pentynyl, hexynyl, and higher isomers, including, e.g., those straight or branched chain hydrocarbons ranging in size from, e.g., about 6 to about 20 carbon atoms, or greater. The preferred size is from 1 to about 6 carbons.

"Aryl," whether used alone, or in compound words such as arylalkyl, aryloxy or arylthio, represents: (i) an optionally substituted mono- or polycyclic aromatic carbocyclic moiety, e.g., of about 6 to about 20 carbon atoms, such as phenyl, naphthyl or fluorenyl; or, (ii) an optionally substituted partially saturated polycyclic carbocyclic aromatic ring system in which an aryl and a cycloalkyl or cycloalkenyl group are fused together to form a cyclic structure such as a tetrahydronaphthyl, indenyl or indanyl ring. The preferred number of carbons in an aryl group ranges from 6 to about 10.

"Cycloalkyl," represents a mono- or polycarbocyclic ring system of varying sizes, e.g., from about 3 to about 20 carbon atoms, e.g., cyclopropyl, cyclobutyl, cyclopentyl, cyclohexyl or cycloheptyl. The term cycloalkyloxy represents the same groups linked through an oxygen atom such as cyclopentyloxy and cyclohexyloxy. The term cycloalkylthio represents the same groups linked through a sulfur atom such as cyclopentylthio and cyclohexylthio. The preferred number of carbons in a cycloalkyl group ranges from 3 to about 7.

"Alkylcycloalkyl," represents an alkyl substitution on a cycloalkyl moiety. Examples include 4-methylcyclohexyl and isopropylcyclopentyl. The preferred number of carbons in an alkylcycloalkyl group ranges from about 4 to about 12.

"Cycloalkenyl," represents an unsaturated mono- or polycarbocyclic ring system of 3 to 10 carbons, such as cyclopentenyl and cyclohexenyl. The preferred number of carbons in a cycloalkenyl group ranges from about 5 to about 7.

The term "acyl," whether used either alone, or in compound words such as alkenylacyl and arylacyl represents the radical formed by removing the hydroxyl group from an organic acid. Acyl includes: alkanoyl, aroyl, heteroaroyl. "Alkanoyl" means the group RCO where R is alkyl, examples include formyl, acetyl, propionyl, and the different butyryl, valeryl, caproyl and higher isomers. "Aroyl" means an acyl group derived from an aromatic acid. "Heteroaroyl" means the group RCO where R is heterocyclyl. Preferred acyl groups contain from 1 to about 10 carbons.

The term, "carbamoyl" represents the group $R_2N$—CO wherein R is H, alkyl, aryl, or heteroaryl. Examples include N-methylcarbamoyl, and N,N-dimethylcarbamoyl.

"Thiocarbamoyl" represents a group $R_2N$—CS where R is H, alkyl, aryl or heteroaryl, examples include N-methylthiocarbamoyl, and N,N-dimethylthiocarbamoyl.

"Aminothiocarbonyl" represents a group $R_2N$—CS where R is H, alkyl, aryl or heteroaryl. Examples include aminothioformyl, methylaminothioformyl, dimethylaminothioformyl, diethylaminothioformyl, benzylaminothioformyl, phenylaminothioformyl.

The term "halo," either alone or in compound words such as "haloalkyl," represents fluorine, chlorine, bromine or iodine. Further, when used in compound words such as "haloalkyl" said alkyl may be partially halogenated or fully substituted with halogen atoms which may be the same or different. Examples of haloalkyl include $CH_2CH_2F$, $CF_2CF_3$ and $CH_2CHFCl$. Examples of "haloalkenyl" include $Cl_2C=CHCH_2$ and $CF_3CH_2CH=CHCH_2$. Examples of "haloalkynyl" include $HC≡CCHCl$, $CF_3C≡C$, $CCl_3C≡C$ and $FCH_2C≡CCH_2$. Examples of "haloalkoxy" include $CF_3O$, $CCl_3CH_2O$, $CF_2CH_2CH_2O$ and $CF_3CH_2O$. Examples of "haloalkylthio" include $CCl_3S$, $CF_3S$, $CCl_3CH_2S$ and $CH_2ClCH_2ClCH_2CH_2S$. Examples of "haloalkylsulfonyl" include $CF_3SO_2$, $CCl_3SO_2$, $CF_3CH_2SO_2$ and $CF_3CF_2SO_2$.

"Heterocyclyl" represents a group comprising a 3 to 10 membered, preferably 5 to 8 membered, ring containing one to three hetero atoms such as oxygen, nitrogen or sulfur, which ring may be substituted and/or carry fused rings. Examples of such groups include, pyrrolidinyl, morpholinyl, thiomorpholinyl, or fully or partially hydrogenated thienyl, furanyl, pyrrolyl, thiazolyl, oxazoyl, oxazinyl, thiazinyl, pyridinyl and azepinyl. The heterocyclyl group may be aromatic in which case it may be referred to herein as a "heteroaryl" group. Examples of heteroaryl include pyridyl, furanyl, thienyl, pyrrolyl, pyrazoyl, benzthiazolyl, indolyl, benzofuranyl, benzothiophenyl, pyrazinyl, quinoyl, pyrimidinyl.

"Alkoxy" represents an alkyl group linked to the rest of the molecule via an oxygen atom, for example methoxy, ethoxy, n-propoxy, iso-propyloxy, and the different butyloxy, pentyloxy, hexyloxy and higher isomers. The preferred number of carbons in an alkoxy group ranges from 1 to about 6.

"Alkenyloxy" represents straight chain or branched alkenyloxy moieties. Examples of alkenyloxy include $CH_2=CHCH_2O$, $(CH_3)_2C=CHCH_2O$, $(CH_3)CH=C(CH_3)CH_2O$ and $CH_2C=CHCH_2CH_2O$. The preferred number of carbons in an alkenyloxy group ranges from 2 to 6.

"Aryloxy" represents an aryl group linked to the rest of the molecule via an oxygen atom, for example phenoxy. "Aryloxyalkyl" denotes aryloxy substitution on alkyl. "Alkyloxyaryl" denotes alkoxy substitution on aryl.

"Arylalkoxy" denotes aryl substitution on an alkoxy group, e.g. benzyloxy and 2-phenylethoxy.

"Alkoxycarbonyl" represents a group $ROC=O$ where R is alkyl. Examples of "alkoxycarbonyl" include $CH_3C(=O)$, $CH_3CH_2C(=O)$, $CH_3CH_2CH_2C(=O)$, $(CH_3)_2CHOC(=O)$ and the different butoxy-, pentoxy-, hexyloxycarbonyl and higher isomers. The preferred range of carbons for an alkoxycarbonyl group is from 2 to about 8.

"Alkylthio" denotes alkyl groups linked to the rest of the molecule via a sulfur atom, for example methylthio, ethylthio, n-propylthio, iso-propylthio, and the different butylthio, pentylthio, hexylthio and higher isomers.

"Sulfonyl" represents an $—SO_2R$ group that is linked to the rest of the molecule through a sulfur atom.

"Alkylsulfonyl" represents an $—SO_2$-alkyl group in which the alkyl group is as defined supra.

"Arylsulfonyl" represents an $—SO_2$-aryl group in which the aryl group is as defined supra.

"Cyano" represents a $—CN$ moiety.

The term "prodrug" as used herein refers to a compound which is convertible in use, e.g., on an environmental surface and/or in vivo, by metabolic means or other processes (e.g., by hydrolysis) to one of the compounds of the invention, e.g., a compound of Formula 1. For example, derivatization of the compound of Formula 1, when $R_1$ is hydrogen, is contemplated to provide a compound convertible by hydrolysis in vivo to the parent molecule. In certain optional embodiments, delivery of the active compound in prodrug form achieves improved delivery of the inventive compound by improving its physicochemical/pharmacokinetic properties, e.g., by enhancing systemic absorption, delaying clearance or breakdown, in vivo.

A parasite "infestation" refers to the presence of parasites in numbers that pose a risk to humans or animals. The presence can be in the environment, e.g., in human or animal house, and surrounding property or structures, on agricultural crops or other types of plants, in animal bedding, on the skin or fur of an animal, etc. When the infestation that is referred to is within an animal, e.g., in the blood or other internal tissues, the term infestation is also intended to be synonymous with the term, "infection," as that term is generally understood in the art, unless otherwise stated.

"Metaphylaxis" is a type of prevention, and defined herein as the timely mass medication of an entire group of animals (e.g., through administering a compound of the present invention to the animal subject, and/or applying the compound to at least a portion of the local environment of that animal, see below) to eliminate and/or minimize an expected outbreak of a disease and/or infestation. A metaphylaxis claim also can be termed as a "High-Risk Claim".

An "effective amount," is the amount or quantity of a compound identified herein that is required to alleviate or reduce parasite numbers in a sample of such parasites, and/or to reduce the numbers of such parasites in and/or on an animal, and/or to inhibit the development of parasite infestation in or on an animal, in whole or in part. This amount is readily determined by observation or detection of the parasite numbers both before and after contacting the sample of parasites with the compound, directly and/or indirectly, e.g., by contacting articles, surfaces, foliage, or animals with the compound. For an in vivo administration of the compound according to the invention; an effective amount is synonymous with a "pharmaceutically effective amount," which is the dose or amount that treats or ameliorates symptoms and/or signs of parasite infection or infestation by the treated animal. This later amount is also readily determined by one of ordinary skill in the art, e.g., by observing or detecting changes in clinical condition or behavior of treated animals, as well as by observing or detecting relative changes in parasite numbers after such treatment. Whether the compound is applied in vivo or ex vivo, the treatment is effective when the parasite count is reduced, after a first application or administration, by an amount ranging from 5% to about 100%. Alternatively, the reduction in parasite count ranges from about 10% to about 95%, relative to the parasite count in an equivalent untreated sample.

The compounds identified herein can exist as one or more stereoisomers. The various stereoisomers include enantiomers, diastereomers and geometric isomers. Those skilled in the art will appreciate that one stereoisomer may be more active than the other(s). In addition, the skilled artisan would know how to separate such stereoisomers. Accordingly, the present invention comprises mixtures, individual stereoisomers, and optically active mixtures of the compounds described herein. In particular, Formula 1 illustrates the Z configuration, but it should be appreciated that these derivatives may also exist in the E configuration, and it is contemplated that the identified compounds optionally include E and Z isomers, and mixtures of these isomers.

Certain compounds of the present invention will be acidic in nature and can form pharmaceutically acceptable metal, ammonium and organic amine salts. The metal salts include alkali metal (e.g., lithium, sodium and potassium), alkaline earth metal (e.g., barium, calcium and magnesium) and heavy metal (e.g., zinc and iron) salts as well as other metal salts such as aluminum. The organic amine salts include the salts of pharmaceutical acceptable aliphatic (e.g., alkyl), aromatic and heterocyclic amines, as well as those having a mixture of these types of structures.

Amines useful in preparing the salts of the compounds identified herein can be primary, secondary or tertiary and preferably contain not more than 20 carbon atoms. The salts are prepared by contacting the acid form with a sufficient amount of the appropriate base to produce a salt in the conventional manner. The acid forms may be regenerated by treating the salt with a suitable dilute aqueous acid solution. The acid forms differ from their respective salt forms somewhat in certain physical properties, such as solubility in polar solvents, but the salts are otherwise equivalent to their respective acid forms for the purposes of the invention.

All such salts are intended to be pharmaceutically acceptable within the scope of the invention and all salts are considered equivalent to the acid form for the purposes of the invention.

The compounds of the invention, and the compounds employed in the methods of the invention can also form stable complexes with solvent molecules that remain intact after the non-complexed solvent molecules are removed from the compounds. These complexes are referred to herein as "solvates". Solvates of the compounds of the present invention are also included in the present invention. In a particular embodiment, the solvent molecule is water, and the solvate is termed a hydrate.

For all of the methods and new compounds described herein, it is also contemplated that the identified compounds are readily employed in combination with one or more art-known agents for killing or controlling various types of parasites, e.g., including all of the ecto- and endoparasites described herein. Thus, although the inventive compounds and methods are preferred over previously known agents and methods of using previously known agents, in certain optional embodiments they are contemplated to be employed in combination, simultaneously, or sequentially (e.g. in the same composition or in separate compositions), with other art-known agents or combinations of such art-known agents employed for killing or controlling various types of pests.

These additional agents include, for example, art-known anthelmintics, such as, for example, avermectins (e.g. ivermectin, moxidectin, milbemycin), benzimidazoles (e.g. albendazole, triclabendazole), salicylanilides (e.g. closantel, oxyclozanide), substituted phenols (e.g. nitroxynil), pyrimidines (e.g. pyrantel), imidazothiazoles (e.g. levamisole) and praziquantel.

Additional art-known agents for killing or controlling pests include the organophosphate pesticides. This class of pesticides has very broad activity, e.g. as insecticides and, in certain instances, anthelminitic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion, phosalone, to name but a few such compounds. It is also contemplated to include combinations of the inventive methods and compounds with carbamate type pesticides, including, e.g., carbaryl, carbofuran, aldicarb, molinate, methomyl, carbofuran, etc., as well as combinations with the organochlorine type pesticides. It is further contemplated to include combinations with biological pesticides, including e.g. repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *bacillus thuringensis*, chlorobenzilate, formamidines, (e.g. amtitaz), copper compounds, e.g., copper hydroxide, cupric oxychloride sulfate, cyfluthrin, cypermethrin, dicofol, endosulfan, esenfenvalerate, fenvalerate, lambda-cyhalothrin, methoxychlor and sulfur.

In addition, for all of the methods and new compounds described herein, it is further contemplated that the identified compounds can be readily employed in combination with syngergists such as piperonyl butoxide (PBO) and triphenyl phosphate (TPP); and/or with Insect Growth Regulators (IGRs) and Juvenile Hormone Analogues (JHAs) such as diflubenzuron, triflumuron, fluazuron, cyromazine, methoprene, etc., thereby providing both initial and sustained control of parasites (at all stages of insect development, including eggs) on the animal subject, as well as within the environment of the animal subject.

Combinations with cyclodienes, ryania, KT-199 and/or older art-known anti-helminth agents, such as avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole), praziquantel and some organophosphates such as naphthalophos and pyraclofos, are also contemplated to be employed in such combinations.

In particular, additional antiparasitic compounds useful within the scope of the present invention are preferably comprised of the class of avermectin compounds. As stated above, the avermectin family of compounds is a series of very potent antiparasitic agents known to be useful against a broad spectrum of endoparasites and ectoparasites in mammals.

A preferred compound for use within the scope of the present invention is ivermectin. Ivermectin is a semi-synthetic derivative of avermectin and is generally produced as a mixture of at least 80% 22,23-dihydroavermectin $B1_a$ and less than 20% 22,23-dihydroavermectin $B1_b$. Ivermectin is disclosed in U.S. Pat. No. 4,199,569, hereby incorporated by reference. Ivermectin has been used as an antiparasitic agent to treat various animal parasites and parasitic diseases since the mid-1980's.

Abamectin is an avermectin that is disclosed as avermectin B1a/B1 b in U.S. Pat. No. 4,310,519, which is hereby incorporated by reference in its entirety. Abamectin contains at least 80% of avermectin $B1_a$ and not more than 20% of avermectin $B1_b$.

Another preferred avermectin is Doramectin also known as 25-cyclohexyl-avermectin $B_1$. The structure and preparation of Doramectin, is disclosed in U.S. Pat. No. 5,089,480, which is hereby incorporated by reference in its entirety.

Another preferred avermectin is Moxidectin. Moxidectin, also known as LL-F28249 alpha is known from U.S. Pat. No. 4,916,154, which is hereby incorporated by reference in its entirety.

Another preferred avermectin is Selamectin. Selamectin is 25-cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a Milbemycin producing strain of *Streptomyces*. The microorganism, the fermentation conditions and the isolation procedures are more fully described in U.S. Pat. Nos. 3,950,360 and 3,984,564.

Emamectin (4"-deoxy-4"-epi-methylaminoavermectin $B_1$), which can be prepared as described in U.S. Pat. Nos. 5,288,710 or 5,399,717, is a mixture of two homologues, 4"-deoxy-4"-epi-methylaminoavermectin B1a and 4"-deoxy-4"-epi-methylaminoavermectin B1b. Preferably, a salt of Emamectin is used. Non-limiting examples of salts of Emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is Emamectin benzoate.

Eprinomectin is chemically known as 4"-epi-Acetylamino-4"-deoxy-avermectin $B_1$. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The composition of the present invention optionally comprises combinations of one or more of the following antiparasite compounds.

The antiparasite imidazo[1,2-b]pyridazine compounds as described by U.S. application Ser. No. 11/019,597, filed on Dec. 22, 2004, incorporated by reference herein.

The antiparasite 1-(4-mono and di-halomethylsulphonylphenyl)-2-acylamino-3-fluoropropanol compounds, as described by U.S. application Ser. No. 11/018,156, filed on Dec. 21, 2004, incorporated by reference herein.

The antiparasite trifluoromethanesulfonanilide oxime ether derivative compounds, as described by U.S. application Ser. No. 11/231,423, filed on Sep. 21, 2005, incorporated by reference herein.

The antiparasite n-[(phenyloxy)phenyl]-1,1,1-trifluoromethanesulfonamide and n-[(phenylsulfanyl)phenyl]-1,1,1-trifluoromethanesulfonamide derivatives, as described by U.S. Provisional Application Ser. No. 60/688,898, filed on Jun. 9, 2005, incorporated by reference herein.

The compositions of the present invention may also further comprise a flukicide. Suitable flukicides include, for example, Triclabendazole, Fenbendazole, Albendazole, Clorsulon and Oxibendazole. It will be appreciated that the above combinations may further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g., in a combined composition and/or in separate dosage forms. Art-known antibiotics suitable for this purpose include, for example, those listed hereinbelow.

One useful antibiotic is Florfenicol, also known as D-(threo)-1-(4-methylsulfonylphenyl)-2-dichloroacetamido-3-fluoro-1-propanol. Another preferred antibiotic compound is D-(threo)-1-(4-methylsulfonyphenyl)-2-difluoroacetamido-3-fluoro-1-propanol. Another useful antibiotic is Thiamphenicol. Processes for the manufacture of these antibiotic compounds, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361, hereby incorporated by reference. Other florfenicol analogs and/or prodrugs have been disclosed and such analogs also can be used in the compositions and methods of the present invention [see e.g., U.S. Patent Application Publication No: 2004/0082553, and U.S. patent application Ser. No. 11/016,794, both of which are hereby incorporated by reference in their entireties]. When the antibiotic compound is Florfenicol, the concentration of Florfenicol typically is from about 10% to about 50% w/v, with the preferred level between about 20% and about 40% w/v, even more preferred being at least about 30% w/v.

Another useful antibiotic compound is Tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695, hereby incorporated by reference. Also disclosed in U.S. Pat. No. 4,820,695 is an injectable, aqueous formulation comprising 50% (by volume) propylene glycol, 4% (by volume) benzyl alcohol, and 50 to 500 mg/ml of active ingredient. Tilmicosin may be present as the base or as a phosphate. Tilmicosin has been found to be useful in treatment of respiratory infections, particularly *Pasteurella haemolytica* infections in cattle when administered by injection over a 4 day treatment period. Accordingly, Tilmicosin may be used in treatment of, for example, neonatal calf pneumonia and bovine respiratory disease. When Tilmicosin is present, it is present in an amount of about 1% to about 50%, preferably 10% to about 50%, and in a particular embodiment, 30%.

Another useful antibiotic for use in the present invention is Tulathromycin. Tulathromycin has the following chemical structure.

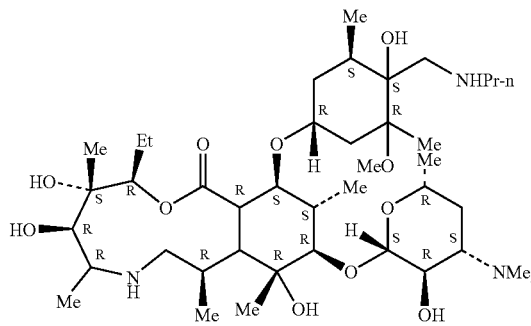

Tulathromycin may be identified as 1-oxa-6-azacyclopentadecan-15-one, 13-[(2,6-dideoxy-3-C-methyl-3-O-methyl-4-C-[(propylamino)methyl]-alpha-L-ribo-hexopyranosyl]oxy]-2-ethyl-3,4,10-trihydroxy-3,5,8,10,12,14-hexamethyl-11-[[3,4,6-trideoxy-3-(dimethylamino)-beta-D-xylo-hexopyranosyl]oxy]-, (2R, 3S, 4R, 5R, 8R, 10R, 11R, 12S, 13S, 14R). Tulathromycin may be prepared in accordance with the procedures set forth in U.S. Patent Publication No. 2003/0064939 A1, which is hereby incorporated by reference in its entirety. Tulathromycin may be present in injectable dosage forms at concentration levels ranging from about 5.0% to about 70% by weight. Tulathromycin is most desirably administered in dosages ranging from about 0.2 mg per kg body weight per day (mg/kg/day) to about 200 mg/kg/day in single or divided doses (i.e., from 1 to 4 doses per day), and more preferably 1.25, 2.5 or 5 mg/kg once or twice weekly, although variations will necessarily occur depending upon the species, weight and condition of the subject being treated. Tulathromycin may be present in injectable dosage forms at concentration levels ranging from about 5.0% to about 70% by weight.

Further antibiotics for use in the present invention include the cephalosporins such as, for example, Ceftiofur, Cefquinome, etc. The concentration of the cephalosporin in the formulation of the present invention optionally varies between about 1 mg/ml to 500 mg/ml.

Another useful antibiotic includes the fluoroquinolones, such as, for example, Enrofloxacin, Danofloxacin, Difloxacin, Orbifloxacin and Marbofloxacin. In the case of Enrofloxacin, it may be administered in a concentration of about 100 mg/ml. Danofloxacin may be present in a concentration of about 180 mg/ml.

Other useful macrolide antibiotics include compounds from the class of ketolides, or, more specifically, the azalides. Such compounds are described in, for example, U.S. Pat. Nos. 6,514,945, 6,472,371, 6,270,768, 6,437,151 and 6,271,255, and 6,239,112, 5,958,888, and 6,339,063 and 6,054,434, all of which are hereby incorporated by reference in their entireties.

Other useful antibiotics include the tetracyclines, particularly Chlortetracycline and Oxytetracycline. Other antibiotics may include p-lactams such as penicillins, e.g., Penicillin, Ampicillin, Amoxicillin, or a combination of Amoxicillin with Clavulanic acid or other beta lactamase inhibitors Additionally, the present invention optionally includes a composition for the treatment of a microbial and parasitic infection in an animal that comprises one or more of the above-listed antibiotics admixed and/or in combination with one or more of the inventive compounds, and an optional carrier and/or excipient.

Further, it is also contemplated that the inventive methods and compounds be advantageously employed in combination, simultaneously or sequentially, with art-known animal health remedies e.g., trace elements, vitamins, anti-inflammatories, anti-infectives and the like, in the same or different compositions.

Inventive Compounds and Compounds Employed In The Inventive Methods

In one preferred embodiment of the invention, the inventive methods include contacting susceptible ecto- or endoparasites with an effective amount of a 2-phenyl-3-(1H-pyrrol-2-yl)acrylonitrile compound of Formula 1, or a pharmaceutically acceptable salt thereof or a solvate thereof.

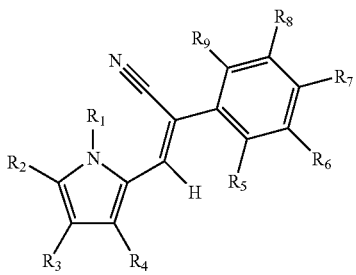

Formula 1

In Formula 1:

$R_1$ is H, lower alkyl, alkoxyalkyl, alkoxyalkoxyalkyl, 1,1-(dialkoxy)alkyl (such as $(EtO)_2CH—$), 1-alkoxy-1-alkylmethyl (such as $EtOCH(CH_3)—$), aroyl, alkanoyl, arylalkyl, alkoxycarbonyl, arylalkoxycarbonyl, arylsulfonyl, alkylarylsulfonyl, alkylalkenyl, N-alkylcarbamoyl, N,N-dialkylcarbamoyl, N-alkylthiocarbamoyl], N,N-dialkylthiocarbamoy, wherein the above groups are optionally substituted; $R_2$-$R_9$ are independently selected from H, nitro, cyano, halo, alkyl, aryl, cycloalkyl, cycloalkenyl, alkylcycloalkyl, alkylcycloalkenyl, cycloalkylalkyl, arylalkyl, aryloxyalkyl, arylthioalkyl, haloalkyl, haloalkenyl, haloalkynyl, haloaryl, halocycloalkyl, alkoxy, alkenyloxy, alkynyloxy, aryloxy, cycloalkyloxy, cycloalkenyloxy, alkylcycloalkyloxy, alkylcycloalkenyloxy, cycloalkylalkyloxy, arylalkoxy, aryloxyalkoxy, arylthioalkyloxy, haloalkoxy, haloalkenyloxy, haloalkynyloxy, haloaryloxy and halocycloalkoxy. Optionally, $R_5$ and $R_6$ or $R_6$ and $R_7$ are connected in a fused ring consisting of 5-7 members. In addition, the above groups are optionally substituted.

Some preferred methods in this aspect of the invention include those employing compounds of Formula 1, wherein:

$R_1$ is H, lower alkyl, alkoxyalkyl, alkoxyalkoxyalkyl, 1,1-(dialkoxy)alkyl (such as $(EtO)_2CH—$), 1-alkoxy-1-alkylmethyl (such as $EtOCH(CH_3)—$), aroyl, alkanoyl, arylalkyl, alkoxycarbonyl, arylalkoxycarbonyl, arylsulfonyl, alkylarylsulfonyl, alkylalkenyl, N-alkylcarbamoyl, N,N-dialkylcarbamoyl, N-alkylthiocarbamoyl], N,N-dialkylthiocarbamoyl, wherein the above groups are optionally substituted;

$R_2$-$R_9$ are independently selected from H, nitro, cyano, halo, alkyl, alkenyl, alkynyl, aryl, cycloalkyl, haloalkyl, haloalkenyl, haloalkynyl, haloaryl, halocycloalkyl, alkoxy, alkenyloxy, aryloxy, cycloalkyloxy, arylalkoxy, aryloxyalkoxy, haloalkoxy, haloalkenyloxy, haloaryloxy, alkylthio, arylthio, cycloalkylthio, arylalkylthio, aryloxyalkylthio, additionally $R_5$ and $R_6$ or $R_6$ and $R_7$ can be connected in a fused ring consisting of 5-7 members, or a pharmaceutically acceptable salt thereof or a solvate thereof. In addition, the above groups are optionally substituted.

Further preferred compounds or a pharmaceutically acceptable salt thereof or a solvate thereof in this aspect of the invention include those of Formula 1, wherein:

$R_1$ is H, lower alkyl, alkoxyalkyl, alkoxyalkoxyalkyl, 1,1-(dialkoxy)alkyl (such as $(EtO)_2CH—$), 1-alkoxy-1-alkylmethyl (such as $EtOCH(CH_3)—$), aroyl, alkanoyl, arylalkyl, alkoxycarbonyl, arylalkoxycarbonyl, arylsulfonyl, alkylarylsulfonyl, alkylalkenyl, N-alkylcarbamoyl, N,N-dialkylcarbamoyl, N-alkylthiocarbamoyl], N,N-dialkylthiocarbamoyl, the above groups are optionally substituted;

$R_2$-$R_4$ are independently selected from H, halo, alkyl, alkoxy, the above groups are optionally substituted; and $R_5$-$R_9$ are independently selected from H, nitro, cyano, halo, alkyl, alkenyl, alkynyl, aryl, cycloalkyl, haloalkyl, haloaryl, halocycloalkyl, alkoxy, alkenyloxy, aryloxy, cycloalkyloxy, arylalkoxy, haloalkoxy and haloaryloxy. Optionally, $R_5$ and $R_6$ or $R_6$ and $R_7$ are connected in a fused ring consisting of 5-7 members. In addition, the above groups are optionally substituted.

Some preferred methods in this aspect of the invention include those employing 2-phenyl-3-(1H-pyrrol-2-yl)acrylonitrile compounds of Formula 1 wherein:

$R_1$ is selected from the group consisting of H, $CH_3$, EOM, DOM, propanoyl, benzyl, $Et_2NC(O)$, Boc, 2-methyl prop-1-enyl, benzoyl, tosyl, $Me_2NC(S)$, MeOC(O) and Cbz;

$R_2$ is H or Cl;

$R_3$ is selected from the group consisting of H, Cl or Br;

$R_4$ is H;

$R_5$ is selected from the group consisting of H, Cl, Br $CH_3$, nitrile, $CF_3$, phenyl and OMe;

$R_6$ is selected from the group consisting of H, Cl, F, Br, $CF_3$, O-phenyl and $CH_3$;

$R_7$ is selected from the group consisting of H, Cl, F, $CH_3$, methoxy, t-butyl, phenyl, and nitrile; and $R_8$ and $R_9$ are independently, H, halo or $CF_3$.

Optionally, $R_5$ and $R_6$ or $R_6$ and $R_7$ are aryl are linked by a —CH═CH—CH═CH-moiety, so that $R_5$ and $R_6$ or $R_6$ and $R_7$ form a naphthyl moiety.

Some compounds that are particularly preferred in the inventive methods, and several new compounds based on Formula 1, are set forth in Tables 1a and 1b, as follows.

TABLE 1a

Specific Examples of Formula 1

| No | $R_1$ | $R_3$ | $R_2$ | $R_5$ | $R_6$ | $R_7$ | $R_8$ | $R_9$ |
|---|---|---|---|---|---|---|---|---|
| 1 | H | H | H | H | Cl | H | H | H |
| 2 | H | H | H | H | H | Cl | H | H |
| 3 | H | Cl | Cl | H | H | Cl | H | H |
| 4 | H | H | H | H | H | $CF_3$ | H | H |
| 5 | $CH_3$ | H | H | H | Cl | H | H | H |
| 6 | $CH_3$ | H | H | H | H | Cl | H | H |
| 7 | EOM | H | H | H | H | Cl | H | H |
| 8 | EOM | H | H | H | H | $CF_3$ | H | H |
| 9 | H | H | H | H | $CF_3$ | H | H | H |
| 10 | H | H | H | H | F | H | H | H |
| 11 | H | Br | H | H | H | $CF_3$ | H | H |

TABLE 1a-continued

Specific Examples of Formula 1

| No | R1 | R3 | R2 | R5 | R6 | R7 | R8 | R9 |
|---|---|---|---|---|---|---|---|---|
| 12 | H | Br | H | H | CF3 | H | H | H |
| 13 | H | H | H | Cl | H | Cl | H | H |
| 14 | H | H | H | H | H | OMe | H | H |
| 15 | H | H | H | H | H | t-butyl | H | H |
| 16 | H | H | H | CH3 | H | H | H | H |
| 17 | H | H | H | H | H | H | H | H |
| 18 | H | H | H | H | H | phenyl | H | H |
| 20 | H | H | H | H | H | nitrile | H | H |
| 21 | CH3 | H | H | H | H | CF3 | H | H |
| 22 | CH3 | H | H | H | CF3 | H | H | H |
| 23 | H | Br | H | H | H | Cl | H | H |
| 24 | H | H | H | Cl | H | H | H | H |
| 25 | H | H | H | F | H | H | H | H |
| 26 | H | H | H | H | H | CH3 | H | H |
| 27 | H | H | H | H | Cl | Cl | H | H |
| 28 | H | H | H | H | H | F | H | H |
| 29 | H | Br | H | H | Cl | Cl | H | H |
| 30 | H | Br | H | H | H | F | H | H |
| 31 | H | Br | H | H | F | H | H | H |
| 33 | H | H | H | H | H | Br | H | H |
| 35 | H | H | H | H | H | H | H | H |
| 36 | H | H | H | H | H | I | H | H |
| 37 | H | H | H | nitrile | H | H | H | H |
| 38 | H | H | H | Br | H | H | H | H |
| 39 | H | H | H | H | Br | H | H | H |
| 40 | H | H | H | H | H | NO2 | H | H |
| 41 | DOM | H | H | H | H | Cl | H | H |
| 42 | DOM | H | H | H | H | nitrile | H | H |
| 43 | DOM | H | H | H | H | H | H | F |
| 44 | DOM | H | H | H | H | NO2 | H | H |
| 45 | DOM | H | H | H | Cl | H | H | H |
| 46 | DOM | H | H | H | F | H | H | H |
| 47 | H | H | H | H | F | F | H | H |
| 48 | H | H | H | F | H | Cl | H | H |
| 49 | EOM | H | H | H | H | F | H | H |
| 50 | EOM | H | H | nitrile | H | H | H | H |
| 51 | EOM | H | H | H | H | Br | H | H |
| 52 | EOM | H | H | Cl | H | H | H | Cl |
| 54 | EOM | H | H | Cl | H | H | H | H |
| 55 | EOM | H | H | F | H | H | H | H |
| 56 | EOM | H | H | H | Cl | Cl | H | H |
| 57 | EOM | H | H | CF3 | H | H | H | H |
| 58 | EOM | H | H | H | Br | H | H | H |
| 59 | EOM | H | H | H | CF3 | H | CF3 | H |
| 60 | EOM | H | H | F | H | F | H | H |
| 61 | EOM | H | H | F | H | H | H | F |
| 62 | EOM | H | H | H | F | F | H | H |
| 63 | EOM | H | H | H | CH3 | H | H | H |
| 64 | EOM | H | H | H | H | CH3 | H | H |
| 67 | H | H | H | Cl | H | H | H | F |
| 68 | H | H | H | H | CF3 | H | CF3 | H |
| 69 | H | H | H | F | H | F | H | H |
| 70 | H | H | H | F | H | H | H | F |
| 71 | H | H | H | H | OPh | H | H | H |
| 72 | H | H | H | H | CH3 | H | H | H |
| 73 | H | H | H | Br | F | H | H | H |
| 74 | H | H | H | Cl | H | F | H | H |
| 75 | H | H | H | H | H | ethyl | H | H |
| 76 | propanoyl | H | H | H | H | Cl | H | H |
| 77 | benzyl | H | H | H | H | Cl | H | H |
| 78 | Et2NC(O) | H | H | H | H | Cl | H | H |
| 79 | Boc | H | H | H | H | Cl | H | H |
| 80 | 3-M-2-B | H | H | H | H | Cl | H | H |
| 81 | H | H | H | H | Cl | F | H | H |
| 82 | benzoyl | H | H | H | H | Cl | H | H |
| 83 | tosyl | H | H | H | H | Cl | H | H |
| 84 | Me2NC(S) | H | H | H | H | Cl | H | H |
| 85 | MeOC(O) | H | H | H | H | Cl | H | H |
| 86 | Cbz | H | H | H | H | Cl | H | H |
| 87 | H | H | H | H | H | i-propyl | H | H |
| 88 | H | H | H | H | CH3 | CH3 | H | H |
| 89 | H | H | H | Ph | H | H | H | H |
| 90 | H | H | H | CF3 | H | H | H | H |
| 91 | H | H | H | OMe | H | H | H | H |

No = Compound number;
EOM = ethoxymethyl;
DOM = diethoxymethyl;
Boc = tert-butoxycarbonyl;
Cbz = benzyloxycarbonyl;
Et = ethyl;
Me = methyl;
Ph = phenyl;
OMe = methoxy;
3-M-2-B = 3-methyl-2-butenyl;
tosyl = p-toluenesulfonate;
i-propyl = isopropyl; and
R4 is H for Table 1a.

TABLE 1b

Additional Specific Examples of Formula 1

| Compound No. | Name and Structure |
|---|---|
| 19 | 2-(3,4-methylenedioxy)phenyl-3-(1H-pyrrol-2-yl)acrylonitrile |
| 32 | 2-(1-naphthyl)-3-(1H-pyrrol-2-yl)acrylonitrile |
| 34 | 2-(1-naphthyl)-3-(4-bromo-1H-pyrrol-2-yl)acrylonitrile |
| 53 | 2-(2-naphthyl)-3-(1-ethoxymethyl-1H-pyrrol-2-yl)acrylonitrile |

TABLE 1b-continued

Additional Specific Examples of Formula 1

| Compound No. | Name and Structure |
|---|---|
| 65 | 2-(1-naphthyl)-3-(1-ethoxymethyl-1H-pyrrol-2-yl)acrylonitrile |
| 66 | 2-(2-naphthyl)-3-(1H-pyrrol-2-yl)acrylonitrile |

Preparation Of The Compounds

Simply by way of example, and without limitation, the compounds can be prepared using one or more of the reaction schemes and methods described below. Some of the compounds useful in this invention are also exemplified by the preparative examples provided below, which should not be construed to limit the scope of the disclosure.

One preparative method is illustrated by FIG. 1, as Scheme 1. Scheme 1 employs the Knoevenagel condensation reaction of a 1H-pyrrole-2-carbaldehyde derivative of Formula 2 with a phenylacetonitrile derivative of Formula 3, in the presence of an aqueous solution of Triton B as described by of EP 1088811, and sometimes in the additional presence of an alcohol, such as ethanol, as described by J. Org. Chem., 1958, 23, 711.

In more detail, the reaction of Scheme 1 affords phenyl-3-(1H-pyrrol-2-yl)acrylonitrile derivatives of Formula 1, which can be recovered by filtration if a solid, or by extraction using art-known methods. These phenyl-3-(1H-pyrrol-2-yl)acrylonitrile derivatives of Formula 1 are generally obtained as a mixture of E and Z isomers. For convenience the Z isomer is shown in the rendering of Formula 1 illustrated by FIG. 1. Generally, the Z isomer is the major isomer that is formed in these condensation reactions (see *Journal of Heterocyclic Chemistry*, 1986, 23, 1747-1752). The isomeric compounds so produced can be separated by the use of standard chromatographic separations known to practitioners of the art.

In these Knoevenagel condensation reactions, phase transfer catalysts such as crown ethers or tetraalkylammonium halides can be substituted for the Triton B solution.

A further embodiment of this process is the use of high pressure, sealed tubes to increase the speed of the reaction. This is especially useful when the reagents of the types described by Formula 2 and Formula 3 contain substituents that sterically hinder the reaction and decrease the speed of the reaction.

This reaction will proceed when $R_1$=H and when $R_1$ is not H in Formula 2, to produce corresponding derivatives of Formula 1. However, it is preferred to prepare products of Formula 1 wherein $R_1$=H and then subsequently modify the substituent $R_1$ to something other than H. Manipulation of $R_1$ provides one method for modifying the pharmacokinetics of the compounds that are derivatives of Formula 1. In an optional alternative, $R_1$ is selected such that the compound behaves as a prodrug. Suitable groups for derivatization of the NH group of compounds of Formula 1 are, for example, alkyl, alkoxyalkyl, alkylcarbonyloxyalkyl, alkanoyl, aroyl, alkoxycarbonyl, alkylcarbamoyl, dialkylcarbamoyl and arylsulfonyl.

Animals To Be Treated

The present invention provides methods for the prevention and/or treatment of infestation, diseases and/or related disorders caused by, or as a result of, parasites or other pests that are killed or inhibited (e.g., growth-suppressed) by the 2-phenyl-3-(1H-pyrrol-2-yl)acrylonitrile compounds identified herein. The animal is preferably a vertebrate, and more preferably a mammal, avian or fish. Any of the 2-phenyl-3-(1H-pyrrol-2-yl)acrylonitrile compounds identified herein, or a suitable combination of such compounds, may be administered directly to the animal subject and/or indirectly by applying it to the local environment in which the animal dwells (such as bedding, enclosures, or the like). Direct administration includes contacting the skin, fur or feathers of a subject animal with the compounds, or by feeding or injecting the compounds into the animal. Appropriate animal subjects include those in the wild, livestock (e.g., raised for meat, milk, butter, eggs, fur, leather, feathers and/or wool), beasts of burden, research animals, companion animals, as well as those raised for/in zoos, wild habitats and/or circuses.

In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, antelopes, rabbits, and rodents (e.g., guinea pigs, squirrels, rats, mice, gerbils, and hamsters). Avians include *Anatidae* (swans, ducks and geese), *Columbidae* (e.g., doves and pigeons), *Phasianidae* (e.g., partridges, grouse and turkeys) *Thesienidae* (e.g., domestic chickens), *Psittacines* (e.g., parakeets, macaws, and parrots), game birds, and ratites, (e.g., ostriches).

Birds treated or protected by the inventive compounds can be associated with either commercial or noncommercial aviculture. These include e.g., *Anatidae,* such as swans, geese, and ducks, *Columbidae,* e.g., doves and pigeons, such as domestic pigeons, *Phasianidae,* e.g., partridge, grouse and turkeys, *Thesienidae,* e.g., domestic chickens, *Psittacines,* e.g., parakeets, macaws, and parrots, e.g., raised for the pet or collector market, among others.

For purposes of the present invention, the term "fish" shall be understood to include without limitation, the *Teleosti* grouping of fish, i.e., teleosts. Both the *Salmoniformes* order (which includes the *Salmonidae* family) and the *Perciformes* order (which includes the *Centrarchidae* family) are contained within the *Teleosti* grouping. Examples of potential fish recipients include the *Salmonidae* family, the *Serranidae* family, the *Sparidae* family, the *Cichlidae* family, the *Centrarchidae* family, the three-Line Grunt (*Parapristipoma trilineatum*), and the Blue-Eyed Plecostomus (*Plecostomus* spp), among others.

Other animals are also contemplated to benefit from the inventive methods, including marsupials (such as kangaroos), reptiles (such as farmed turtles) and other economically important domestic animals for which the inventive methods are safe and effective in treating or preventing parasite infection or infestation.

In an optional alternative preferred embodiment, the animals to be treated include all animals that will benefit from such treatment, e.g., as enumerated above, but specifically excluding humans.

Crops To Be Treated

The inventive methods are also contemplated to be employed in protecting against agricultural pests that attack plants by application of the 2-phenyl-3-(1H-pyrrol-2-yl)acrylonitrile compounds identified herein. In particular, plants to be protected or treated include crops of economic or other importance, i.e., in agriculture and related endeavors. Agricultural pests contemplated to be controlled by the inventive methods include, for example, insect pests, including those that can attack stored grains. e.g., *Tribolium* sp., *Tenebrio* sp. Other agricultural pests include spider mites, (*Tetranychus* sp.), aphids, *Acyrthiosiphon* sp.; migratory orthopterans such as locusts, and the immature stages of insects that live on plant tissue such as the Southern army worm and Mexican bean beetle larvae.

Further pests of agricultural importance that are contemplated to be treated or controlled by the inventive methods include, e.g., *Acrobasis vaccinii, Agrotis* spp, *Alsophila pometaria, Archips* spp, *Argyrotaenia citrana, A velutinana, Autographa californica, Bacillus thuringiensis, Callopistria floridensis, Choristoneura fumiferana, C occidentalis, C pinus, C rosaceana, Cryptophlebia ombrodelta, Cydia (Laspeyresia) pomonella, C caryana, Dasychira pinicola, Datana ministra, Desmia funeralis, Diatrea saccharalis, Dichocrocis punctiferalis, Dioryctria zimmerman, Ectropis excursaria, Ematurga amitaria, Ennomos subsignaria, Eoreuma loftini, Epiphyas postvittana, Euproctis chrysorrhoea, Grapholita packardi, Hellula rogatalis, Homoeosoma vagella, Hyphantria cunea, Lambdina fiscellaria, Liphophane antennata, Lobesia botrana, Lophocampa maculata, Lymantria dispar, Malacosoma* spp, *Manduca* spp, *Megalopyge opercularis, Mnesampela privata, Orgyia pseudotsugata, O vetusta, Ostrinia nubilalis, Platynota flavedana, P stultana, Pseudaletia unipuncta, Rhopobota naevana, Rhyacionia* spp, *Spodoptera eridania, S exigua, S frugiperda, S ornithogalli, Thaumatopoea pityocampa, Thridopteryx ephemeraeformis, Thyrinzeina arnobia,* and others too numerous to mention.

Crops that can be treated in order to inhibit, kill, remove, treat or prevent infestation with crop-related pests or parasites include, e.g., alfalfa, apples, avocados, blueberries, brassicas, breadfruit, brocolli, bush berries, cabbage, cane berries, cherry, citrus, citrus oil, clover, cole crops, cotton, cucumber, cranberries, currants, apples, eucalyptus, forestry, beet roots and tops, grapes, grapefruit, gooseberries, hay, huckleberries, kiwi fruit, leafy and fruiting vegetables, legumes, lemon, lime, macadamia nuts, mint, orange, ornamentals, peaches, pears, pecans, peppers, plums, pome fruit, potatoes, raspberry, shrubs, soy, starfruit, sugarcane, sunflower, squash, table beets, tangerine, treenuts, trees, turnips, walnuts, the various grain grasses, including corn or maize, wheat, rye, rice, oats, barley, spelt, millet, etc.

Susceptible Parasites

The 2-phenyl-3-(1H-pyrrol-2-yl)acrylonitrile compounds identified herein as useful in practicing the inventive methods are broadly described as endectoparasiticides, and include compounds that are active against ectoparasites (arthropods, acarines, etc.) and endoparasites (helminths, e.g., nematodes, trematodes, cestodes, canthocephalans, etc.), including pests that prey on agricultural crops and stored grains (spider mites, aphids, caterpillars, migratory orthopterans such as locusts). Parasitical protozoa (*Flagellata, Sarcodina Ciliophora,* and *Sporozoa,* etc.) are also contemplated to be treated by the inventive compounds. The 2-phenyl-3-(1H-pyrrol-2-yl)acrylonitrile compounds identified herein are also active against household pests, and particularly against arthropod pests, such as spiders, mites, and insects, including flies, mosquitoes, ants, termites, silverfish, cockroach, clothes moth, and a myriad of beetles and beetle larvae that impact households. Susceptible parasites are listed in greater detail in the following sections.

1. Helminths

The disease or group of diseases described generally as helminthiasis is due to infection of an animal host with parasitic worms known as helminths. Helminthiasis is a prevalent and serious economic problem with domesticated animals such as swine, sheep, horses, cattle, goats, dogs, cats and poultry. Among the Helminths, the group of worms described as nematodes causes widespread and at times serious infection in various species of animals. Nematodes that are contemplated to be treated by the 2-phenyl-3-(1H-pyrrol-2-yl)acrylonitrile compounds identified herein and by the inventive methods include, without limitation, the following genera:

*Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Heterakis, Lagochilascaris, Loa, Mansonella, Muellerius, Nanophyetus, Necator, Nematodirus, Oesophagostomum, Opisthorchis, Ostertagia, Oxyuris, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichonema, Trichostrongylus, Trichuris, Uncinaria,* and *Wuchereria.*

Of the above, the most common genera of nematodes infecting the animals referred to above are *Haemonchus, Trichostrongylus, Ostertagia, Nemaodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Unicinaria, Toxascaris* and *Parascaris.* Certain of these, such as *Nematodirus, Cooperia* and *Oesophagostomum* attack primarily the intestinal tract while others, such as *Haemonchus* and *Ostertagia,* are more prevalent in the stomach while others such as *Dictyocaulus* are found in the lungs. Still other parasites may be located in other tissues such as the heart and blood vessels, subcutaneous and lymphatic tissue and the like. Table 2, below, lists a number of these, by Family and Genus, that are of economic (medical and veterinary) importance.

TABLE 2

| Class | Family | Genus (examples) |
|---|---|---|
| Trematoda | Fasciolidae | *Fasciola* |
| Cestoda | Anoplocephalidae | *Moniezia* |
| " | Dilepididae | *Dipylidium* |
| " | Taeniidae | *Taenia, Echinococcus* |
| Nematoda | Strongyloididae | *Stongyloides* |
| " | Strongylidae | *Strongylus, Oesophagostomum* |
| " | Syngamidae | *Syngamus* |
| " | Trichostrongylidae | *Trichostrongylus, Cooperia, Ostertagia, Haemonchus* |
| " | Heligmonellidae | *Nippostrongylus* |
| " | Dictyocaulidae | *Dictyocaulus* |
| " | Ascarididae | *Ascaris* |

TABLE 2-continued

| Class | Family | Genus (examples) |
|---|---|---|
| " | Toxocaridae | Toxacara |
| " | Oxyuridae | Oxyuris |
| " | Filaridae | Parafilaria |
| " | Onchocercidae | Onchocerca |
| " | Trichinellidae | Trichinella |
| " | Trichuridae | Trichuris |
| " | Capillariidae | Capillaria |

The most common genera of parasites of the gastrointestinal tract of humans are *Ancylostoma, Necator, Ascaris, Strongyloides, Trichinella, Capillaria, Trichuris,* and *Enterobius*. Other medically important genera of parasites which are found in the blood or other tissues and organs outside the gastrointestinal tract are the filarial worms such as *Wuchereria, Brugia, Onchocerca* and *Loa, Dracunculus* and extra intestinal stages of the intestinal worms *Strongyloides* and *Trichinella*.

Numerous other Helminth genera and species are known to the art, and are also contemplated to be treated by the compounds of the invention. These are enumerated in great detail in TEXTBOOK OF VETERINARY CLINICAL PARASITOLOGY, VOLUME 1, HELMINTHS, by E. J. L. Soulsby, Publ. F.A. Davis Co., Philadelphia, Pa.; HELMINTHS, ARTHROPODS AND PROTOZOA (Sixth Ed. of MONNIG'S VETERINARY HELMINTHOLOGY AND ENTOMOLOGY) by E. J. L. Soulsby, Publ. The Williams and Wilkins Co., Baltimore, Md., the contents of both of which are incorporated by reference herein in their entireties.

The parasitic infections known as helminthiasis lead to anemia, malnutrition, weakness, weight loss, severe damage to the walls of the intestinal tract and other tissues and organs and, if left untreated, may result in death of the infected host. The compounds described herein have unexpectedly high activity against these parasites, and in addition are also active against Dirofilaria in dogs, and Namatospiroides, Syphacia, Aspiculuris in rodents. The inventive compounds are also useful as a nematocide for the control of soil nematodes and plant parasites such as *Meloidogyne* spp.

2. Arthropods

It is also contemplated that the inventive compounds are effective against a number of ectoparasites of animals, e.g., arthropod ectoparasites of mammals and birds. Athropods include those summarized in Table 3, as follows.

TABLE 3

Summary Of Taxonomy for Important Arthropod Pests

| Subphylum | Class | Order | Examples |
|---|---|---|---|
| Triobita | Merostomata | Araneae | spiders |
| Cheliceratac helicera and pedipalps | Arachnida | Scorpionida | scorpions |
| | | Acari | mites and ticks |
| Uniramia | Chilopoda | | centipedes |
| | Diplopoda | | millipedes |
| | Pauropoda | | Soft bodied myriapods |
| | Insecta | Hymenoptera | bees, wasps |
| | | Lepidoptera | moths, butterflies |
| | | Hoptera | grasshoppers |
| | | Diptera | true flies |
| | | Hemiptera | true bugs |
| | | Coleoptera | beetles |

Thus, insect pests include, e.g., biting insects, such as flies and mosquitoes, mites, ticks, lice, fleas, true bugs, parasitic maggots, and the like.

Biting insects include, e.g., migrating *diperous* larvae as *Hypoderma* sp. in cattle, *Gastrophilus* in horses, and *Cuterebra* sp. in rodents, as well as biting flies and mosquitoes of all types. For example, bloodsucking adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, the tsetse fly or *Iossina* spp. Parasitic fly maggots include, e.g., the bot fly (*Oestrus ovis* and *Cuterebra* spp.], the blow fly or *Phaenicia* spp., the screwworm or *Cochliomyia hominivorax*, the cattle grub or *Hypoderma* spp., and the fleeceworm. Mosquitoes, include, for example, *Culex* spp., *Anopheles* spp., and *Aedes* spp.

Mites include *Mesostigmata* spp. e.g., mesostigmatids such as the chicken mite, *Dermanyssus gallinae;* itch or scab mites such as *Sarcoptidae* spp. for example, *Sarcoptes scabiei;* mange mites such as *Psoroptidae* spp. including *Chorioptes bovis* and *Psoroptes ovis;* chiggers e.g., *Trombiculidae* spp. for example the North American chigger, *Trombicula alfreddugesi*.

Ticks include, e.g., soft-bodied ticks including *Argasidae* spp. for example *Argas* spp. and *Ornithodoros* spp.; hard-bodied ticks including *Ixodidae* spp., for example *Rhipicephalus sanguineus*, and *Boophilus* spp.

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides* canis) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other arthropod pests and ectoparasites are known to the art, and are also contemplated to be treated by the compounds of the invention. These are enumerated in great detail in MEDICAL AND VETERINARY ENTOMOLOGY, by D. S. Kettle, Publ. John Wiley & Sons, New York and Toronto; CONTROL OF ARTHROPOD PESTS OF LIVESTOCK: A REVIEW OF TECHNOLOGY, by R. O. Drummand, J. E. George, and S. E. Kunz, Publ. CRC Press, Boca Raton, Fla., the contents of both of which are incorporated by reference herein in their entireties.

3. Protozoa

It is also contemplated that the 2-phenyl-3-(1H-pyrrol-2-yl)acrylonitrile compounds identified herein, and the inventive methods, are effective against a number of protozoa endoparasites of animals, including those summarized by Table 4, as follows.

TABLE 4

Exemplary Parasitic Protozoa and Associated Human Diseases

| Phylum | Subphylum | Representative Genera | Human Disease or Disorder |
|---|---|---|---|
| Sarcomastigophora (with flagella, pseudopodia, or both) | Mastigophora (Flagella) | *Leishmania* | Visceral, cutaneous and mucocutaneous Infection |
| | | *Trypansoma* | Sleeping sickness Chagas' disease |
| | | *Giardia* | Diarrhea |
| | | *Trichomonas* | Vaginitis |
| | Sarcodina (pseudopodia) | *Entamoeba* | Dysentery, liver Abscess |
| | | *Dientamoeba* | Colitis |
| | | *Naegleria* and *Acanthamoeba* | Central nervous system and corneal ulcers |
| | | *Babesia* | Babesiesis |
| Apicomplexa (apical complex) | | *Plasmodium* | Malaria |
| | | *Isospora* | Diarrhea |
| | | *Sarcocystis* | Diarrhea |
| | | *Cryptosporidum* | Diarrhea |
| | | *ToxoDlasma* | Toxoplasmosis |
| Microspora | | *Enterocytozoon* | Diarrhea |
| Ciliephora (with cilia) | | *Balantidium* | Dysentery |
| Unclassified | | *Pneumocystis* | Pneumonia |

4. Animal Pests, Generally

Livestock pests to be controlled by the 2-phenyl-3-(1H-pyrrol-2-yl)acrylonitrile compounds identified herein and the inventive methods include parasites identified above as helminths, arthropods and protozoa. In addition, and simply by way of example, a number of agricultural arthropod pests are summarized by Table 5, below, in association with exemplary livestock for which these pests are of economic significance.

TABLE 5

| | |
|---|---|
| Companion animals, e.g., canine, feline. | Flies, fleas, ticks, mites. |
| Horses and other equines. | Horse bots. Horse flies and Deer flies. |
| Cattle | Horn flies, Face flies, Pinkeye and lice. |
| Sheep | Sheep keds (biting flies). |
| Poultry | Lesser Mealworms or Litter beetles. |
| General Pests | Rat-tailed maggots. Moth flies. Ants, including Allegheny mound ants. |

5. Crop Pests

Simply by way of example, a number of agricultural crop pests to be controlled by the 2-phenyl-3-(1H-pyrrol-2-yl) acrylonitrile compounds identified herein, and the inventive methods, are summarized by Table 6, in association with exemplary crops for which these pests are of economic significance.

TABLE 6

| Crop | Parasite or Pest |
|---|---|
| Alfalfa | Blister beetles, generally Clover Root curculio Potato leafhoppers |
| Corn | Armyworms Corn borers, e.g, the Common Stalk borer and the European Corn borer Corn Leaf aphid Cutworm Vegetables Lesser Cornstalk borer Seedcorn Maggots Southwestern Corn Borer Stink bugs Wireworms |
| Soybeans | Beetles, such as the Japanese and the Bean Leaf beetles Cutworms Green cloverworm Seedcorn maggot Soybean podworm |
| Small Grains | Aphids and Barley Yellow Dwarf Armyworms generally, e.g., in small grains. Cereal Leaf beetle Hessian fly Wheat Streak Mosaic virus and the Wheat Curl mite |
| Stored Grain | Beetles, such as the Cadelle beetle and Flour beetle Indianmeal moth Lesser Grain borer |
| Greenhouse Plants | Cyclamen Mites Float Plant pests, generally Springtails |
| General Crop Pests | Aphids Beet armyworm Garden fleahopper Grasshopper, e.g., redlegged, the two-striped, and the differential |

TABLE 6-continued

| Crop | Parasite or Pest |
|---|---|
| | grasshopper. |
| | Japanese beetles |
| | Seed maggots |
| | Two-Spotted Spider mites |
| | Whiteflies |
| Potatoes | Colorado Potato beetle |
| Peppers | Beet Armyworm |
| | European Corn borer |
| | Pepper Maggot |
| Other Vegetables | Cabbage Webworm |
| | Cabbage insects, generally |
| | Squash Vine Borer and Squash Bug |
| Greenhouse | Float Plant pests, generally |
| | Cyclamen mites (e.g., in a Greenhouse) |
| Tree Fruits | Cherry Fruit flies |
| | Codling moth |
| | European Red mite |
| | Green fruitworms |
| | Leafhoppers (e.g, on Apples) |
| | Leaf rollers |
| | Oriental Fruit moth |
| | Peachtree borer |
| | Rosy Apple aphid |
| | San Jose scale |
| | Woolly Apple aphid |
| | Lesser Peachtree borer |
| | Plum vurculio |
| Nuts | Nut weevils |
| | Pecan Insects |
| Grapes | Grape Berry moth |
| | Grape Cane Gallmaker |
| | Grape Cane Girdler |
| | Grape Flea beetle |
| | Grape Insects, generally |
| | phylloxera, e.g., on grapes |
| | Grape Root borer |
| Berries | Rednecked and Raspberry Cane Borers |
| | Root weevils |

6. Household Pests

The inventive compounds are also contemplated to be active against household pests such as the cockroach, *Blatella* sp., clothes moth, *Tineola* sp., carpet beetle, *Attagenus* sp., and the housefly, *Musca domestica*. In particular, susceptible household pests include those that cause sanitary or economic problems in association with residential and office space and materials, as follows.

Ants, including Carpenter ants (*Camponotus* spp), Pavement ants (*Tetramorium caespitum*), Pharaoh ants (*Monomorium pharaonis*), Thief ants (*Solenopsis molesta*), Yellow ants (*Acanthomyops* spp.), Red ants;

Bed Bugs (*Cimex* spp.);

Beetles, e.g., Carpet (*Attagenus* spp.), Longhorned, Flour (*Tribolium* spp.), Drugstore (*Stegobium paniceum*), Elm Leaf, Ladybird (*Harmonia axyridis*);

Old House Borer and Flatheaded Wood Borer, Family *Buprestidae.*, to name but a few;

Boxelder Bug (*Boisea trivittata*);

Carpenter bees;

Centipedes (*Scutigera coleopterata*);

Cockroaches, including, e.g., the American cockroach (*Periplaneta americana*), German cockroach (*Blattella germanica*), Brownbanded cockroach (*Supella longipalpa*), Oriental Cockroach (*Blatta orientalis*), to name but a few.

Earwigs (*Forficula* sp.);

Field crickets;

Flies, including Cluster flies, *Pollenia rudis*; fruit flies, Moth flies, *Psychoda* spp. gnats, including, e.g., the Fungus gnat, *Sciara* spp.

Phorids, Family Phoridae

Millipede (*Looceles reclusa*);

Mites, e.g., Clover mites;

Mosquitoes, e.g., *Culex* spp., *Anopheles* spp., *Aedes* spp.;

Moths, including Clothes (*Tineola* sp., *Tinea* sp.); and Indian Meal (*Plodia interpunctella*);

Psocids (*Liposcellis* sp.);

Silverfish (*Lepisma saccharina*);

Sowbugs;

Spiders, including, e.g., the Black Widow, (*Lactrodectus* spp.), and the Orb Weaver;

Springtails, Order *Collembola*

Ticks, e.g., the American Dog tick, the Lone Star tick (*Amblyomma americanium*); and Wasps, such as the Yellowjacket (*Dolichovespula* spp. and *Vespula* spp.).

Treating and Inhibiting Parasite Infestation of Animals

It will be understood by the artisan that the methods of the present invention are useful in treating diseases and disorders that are known to be associated with the presence of helminths and protozoa, including for example, those listed above, that are present in the tissue or body fluids of animals.

For such infections or infestations, systemic administration is preferred, e.g., administration of the 2-phenyl-3-(1H-pyrrol-2-yl)acrylonitrile compounds identified herein, by a route selected from the oral or rectal route, a parenteral route, e.g., by intraruminal, intramuscular, intravenous, intratracheal, subcutaneous injection, or other type of injection or infusion. A 2-phenyl-3-(1H-pyrrol-2-yl)acrylonitrile compound or suitable mixture of such compounds is optionally administered in the form of a pharmaceutically acceptable oral or parenteral composition, or in the feed or water or other liquid composition, as discussed in greater detail, below.

Generally, good results are obtained with a 2-phenyl-3-(1H-pyrrol-2-yl)acrylonitrile compound as identified herein by the systemic administration of up to about 100 mg per kg of animal body weight. In particular, good results are obtained by the systemic administration of from about 0.001 to 100 mg per kg of animal body weight, or more particularly, from about 0.01 to about 25 mg per kg of animal body weight, such total dose being given at one time or in divided doses over a relatively short period of time such as 1-5 days. With the disclosed inventive compound, excellent control or prevention of such parasites is obtained in animals, by the systemic administration of up to about 50 mg per kg of animal body weight.

In particular, control or prevention of such parasites is obtained by administering a 2-phenyl-3-(1H-pyrrol-2-yl) acrylonitrile compound as identified herein in an amount ranging from about 0.025 to 50 mg per kg of body weight in a single dose, or more particularly, from about 0.025 to about 25 mg per kg of body weight in a single dose, or optionally, from about 1 to about 5 mg per kg in a single dose. Repeat treatments are given as required to combat re-infections and are dependent upon the species of parasite and the husbandry techniques being employed. The techniques for administering these materials to animals are known to the artisan. The exact amount of the 2-phenyl-3-(1H-pyrrol-2-yl)acrylonitrile compound to be given will of course depend on several factors including the specific compound selected, the animal being treated, the parasite(s) infecting the animal, severity of infection, etc. and all such factors being considered by the artisan in calculating the required effective dose without undue experimentation.

In one preferred embodiment, a 2-phenyl-3-(1H-pyrrol-2-yl)acrylonitrile compound as identified herein is administered to an animal in an oral unit dosage form, such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent.

By way of example, drench formulations for immediate administration to animals generally include up to about 50%, by weight, of a 2-phenyl-3-(1H-pyrrol-2-yl)acrylonitrile compound as identified herein. In particular, drench formulations for immediate administration to animals generally include from about 0.0001 to about 50% by weight of the 2-phenyl-3-(1H-pyrrol-2-yl)acrylonitrile compound. Preferred drench formulations contain from about 0.001 to about 10% by weight of the inventive compound. More preferred drench formulations contain from about 0.1 to about 5% by weight of the active compound. The drench capsules and boluses comprise the active ingredient admixed with a carrier vehicle such as starch, talc, magnesium stearate, or di-calcium phosphate. In certain optional embodiments, e.g., for large animals, such drench formulations are applied topically, and provide a surface concentration on the animal that is effective to kill or suppress parasites, e.g., by providing a concentration of the 2-phenyl-3-(1H-pyrrol-2-yl)acrylonitrile compound ranging from about 0.001 $\mu g/cm^2$ to about 1000 $\mu g/cm^2$, or more preferably, from about 0.01 $\mu g/cm^2$ to about 100 $\mu g/cm^2$.

In a further optional embodiment, the 2-phenyl-3-(1H-pyrrol-2-yl)acrylonitrile compounds are formulated as topical compositions, e.g., for spot-on or pour-on administration. Such a topical formulation includes an effective amount of one or more of the 2-phenyl-3-(1H-pyrrol-2-yl)acrylonitrile compounds, with or without other parasiticides or pesticides, in a concentration sufficient to provide an effective amount on topical application, e.g., by providing a concentration of the inventive compound ranging from about 0.001 $\mu g/cm^2$ to about 1000 $\mu g/cm^2$, or more preferably, from about 0.01 $\mu g/cm^2$ to about 100 $\mu g/cm^2$. The topical formulation is optionally admixed with suitable carriers or diluents, including, for example, one or more carriers or emollients such as polyvinylpyrrolidone, polyvinyl alcohols, copolymers of vinyl acetate, and vinylpyrrolidone, polyethylene glycols, benzyl alcohol, mannitol, glycerol, sorbitol, polyoxyethylenated sorbitan esters, lecithin, sodium carboxymethylcellulose, silicone oils, anionic surfactants, cationic surfactants, nonionic surfactants, and amphoteric surfactants, or a mixture of at least two of these agents.

In certain other optional embodiments, the 2-phenyl-3-(1H-pyrrol-2-yl)acrylonitrile compounds may be administered in a controlled release form, e.g., in a subcutaneous slow release formulation, or in the form of a controlled release device affixed to an animal such as a so-called fleacollar. Collars for the controlled release of an insecticide agent for long term protection against flea infestation in a companion animal are art-known, and are described, for example, by U.S. Pat. Nos. 3,852,416, 4,224,901, 5,555,848, and 5,184,573, incorporated herein by reference.

Where it is desired to administer the 2-phenyl-3-(1H-pyrrol-2-yl)acrylonitrile compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the 2-phenyl-3-(1H-pyrrol-2-yl)acrylonitrile compound is to be administered via an animal feedstuff, one or more of the compounds are intimately dispersed in the feed, or used as a top dressing, or in the form of pellets, which may then be added to the finished feed or optionally fed separately.

Alternatively, the 2-phenyl-3-(1H-pyrrol-2-yl)acrylonitrile compound is to be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The selected 2-phenyl-3-(1H-pyrrol-2-yl)acrylonitrile compound is dissolved or suspended in the parenteral formulation for administration; such formulations generally contain from 0.005 to about 25% by weight of the active compound, or optionally, from about 1% to about 10% by weight of the active compound, or from about 1% to about 5% of the active compound (w/w).

The 2-phenyl-3-(1H-pyrrol-2-yl)acrylonitrile compound, as identified herein, is also employed to prevent and treat diseases caused by other parasites, for example, arthropod parasites such as ticks, lice, fleas, mites and other biting insects in domesticated animals, including poultry. These compounds are also effective in treatment of parasitic diseases that occur in other animals including humans. The optimum amount to be employed for best results will, of course, depend upon the particular compound employed, the species of animal to be treated and the type and severity of parasitic infection or infestation.

When the 2-phenyl-3-(1H-pyrrol-2-yl)acrylonitrile compounds described herein are administered as a component of the feed of the animals, or dissolved or suspended in the drinking water, compositions are provided in which the active agent(s) are intimately dispersed in an inert carrier or diluent. An inert carrier is one that will not react with the antiparasitic agent and one that may be administered safely to animals. Preferably, a carrier for feed administration is one that is, or may be, an ingredient of the animal ration.

Suitable compositions include feed pre-mixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active 2-phenyl-3-(1H-pyrrol-2-yl)acrylonitrile compound is intimately dispersed throughout the carrier by methods such as grinding, stirring, milling or tumbling. Compositions containing from about 0.05 to about 5.0%, or from about 0.005 to about 2.0% by weight of the active 2-phenyl-3-(1H-pyrrol-2-yl)acrylonitrile compounds are particularly suitable as feed pre-mixes. Feed supplements, which are fed directly to the animal contain from about 0.0002 to 0.3% by weight of the active 2-phenyl-3-(1H-pyrrol-2-yl)acrylonitrile compound.

Such supplements are added to the animal feed in an amount to give the finished feed the concentration of active compound desired for the treatment and control of parasitic diseases. Although the desired concentration of active 2-phenyl-3-(1H-pyrrol-2-yl)acrylonitrile compounds will vary depending upon the factors mentioned supra as well as upon the particular derivative employed, the compound is usually fed at concentrations of between about 0.0001 to 0.02% or from about 0.00001 to about 0.002% in the feed in order to achieve the desired antiparasitic result.

The inventive methods are also useful in combating agricultural pests that inflict damage upon crops while they are growing or while in storage. The 2-phenyl-3-(1H-pyrrol-2-yl)acrylonitrile compounds are applied using known techniques as sprays, dusts, emulsions and the like, to the growing or stored crops to effect protection from such agricultural pests.

1. Routes of Administration for Animals

As used herein, the terms, "administer" or "administration" refer to the delivery of a 2-phenyl-3-(1H-pyrrol-2-yl)acrylonitrile compound, salt, solvate, or prodrug thereof, or of a pharmaceutical composition containing the 2-phenyl-3-(1H-pyrrol-2-yl)acrylonitrile compound, salt, solvate, or prodrug, to an organism for the purpose of treating or preventing a parasite infestation in animals.

Suitable routes of administration may include, without limitation, oral, rectal, topical, transmucosal, intramuscular, subcutaneous, intramedullary, intrathecal, direct intraventricular, intravenous, intravitreal, intraperitoneal, intranasal, aural or intraocular. The preferred routes of administration are oral and parenteral.

Alternatively, one may administer the 2-phenyl-3-(1H-pyrrol-2-yl)acrylonitrile compounds in a local rather than systemic manner, for example, by preparation as a salve or topically applied formulation that is applied directly to the infected area or by injection of the 2-phenyl-3-(1H-pyrrol-2-yl)acrylonitrile compounds directly into infected tissue. Topical routes of administration include pour-on or spot-on administration, e.g., topically applying a suitable formulation to a localized region, allowing for diffusion of an effective amount of the 2-phenyl-3-(1H-pyrrol-2-yl)acrylonitrile compounds into infected or infested areas. In either case, a sustained release formulation may be used.

Thus, administration of the 2-phenyl-3-(1H-pyrrol-2-yl)acrylonitrile compounds of the invention, solvates thereof, or a pharmaceutically acceptable salt, in pure form or in an appropriate pharmaceutical composition, can be carried out via any of the accepted modes of administration or agents for serving similar utilities. The routes of administration can be any known to those of ordinary skill. The inventive compounds are given to those in need thereof in any art recognized form, i.e., solid, semi-solid, lyophilized powder, or liquid dosage forms, such as for example, tablets, suppositories, pills, soft elastic and hard gelatin capsules, powders, solutions, suspensions, or aerosols, or the like, in unit or multi-dosage forms suitable for simple administration of precise dosages. The compositions will include a conventional pharmaceutical carrier or excipient and a 2-phenyl-3-(1H-pyrrol-2-yl)acrylonitrile compound as the active agent, and, in addition, may include other medicinal agents, pharmaceutical agents, carriers, etc.

For aquatic animal species, e.g., vertebrate fish species, methods of administering the 2-phenyl-3-(1H-pyrrol-2-yl)acrylonitrile compounds include the foregoing, e.g., by injection or by admixing the effective compounds in the feed of farmed fish, and so forth. Method of administering to aquatic animal species also include dipping the fish into water comprising an effective concentration of the 2-phenyl-3-(1H-pyrrol-2-yl)acrylonitrile compounds, spraying the fish with an effective concentration of the compound, while the fish is briefly separated from the water, and so forth.

2. Composition/Formulation for Animals

Pharmaceutical compositions of the present invention may be manufactured by processes well known in the art, e.g., using a variety of well-known mixing, dissolving, granulating, dragee-making, levigating, emulsifying, encapsulating, entrapping or lyophilizing processes. The compositions may be formulated in conjunction with one or more physiologically acceptable carriers comprising excipients and auxiliaries which facilitate processing of the active 2-phenyl-3-(1H-pyrrol-2-yl)acrylonitrile compound into preparations which can be used pharmaceutically. Proper formulation is dependent upon the route of administration chosen.

For injection, including, without limitation, intravenous, intramuscular and subcutaneous injection, the 2-phenyl-3-(1H-pyrrol-2-yl)acrylonitrile compounds may be formulated in aqueous solutions, preferably in physiologically compatible buffers known to those of ordinary skill, as well as other excipients or other materials known to those of ordinary skill. For transmucosal administration, penetrates appropriate to the barrier to be permeated are used in the formulation. Such penetrates are generally known in the art.

For oral administration, the 2-phenyl-3-(1H-pyrrol-2-yl)acrylonitrile compounds can be formulated by combining the active compound with pharmaceutically acceptable carriers well-known in the art. Such carriers enable the 2-phenyl-3-(1H-pyrrol-2-yl)acrylonitrile compounds to be formulated as tablets, pills, lozenges, draggers, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl-methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active 2-phenyl-3-(1H-pyrrol-2-yl)acrylonitrile compound may be dissolved or suspended in suitable liquids, such as fatty oils, liquid paraffin, or liquid polyethylene glycols. Stabilizers also may be added in these formulations.

For administration by inhalation, the 2-phenyl-3-(1H-pyrrol-2-yl)acrylonitrile compounds conveniently can be delivered in the form of an aerosol spray using a pressurized pack or a nebulizer and a suitable propellant, e.g., without limitation, dichlorodifluoro-methane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The 2-phenyl-3-(1H-pyrrol-2-yl)acrylonitrile compounds may also be formulated for parenteral administration, e.g., by bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

The 2-phenyl-3-(1H-pyrrol-2-yl)acrylonitrile compounds may also be formulated in rectal compositions such as suppositories or retention enemas, using, e.g., conventional suppository bases such as cocoa butter or other glycerides.

In addition to the formulations described supra, the 2-phenyl-3-(1H-pyrrol-2-yl)acrylonitrile compounds may also be formulated as a depot preparation. Such long acting formulations may be administered by implantation (for example, subcutaneously or intramuscularly) or by intramuscular or subcutaneous injection. 2-phenyl-3-(1H-pyrrol-2-yl)acrylonitrile compounds may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

Additionally, the 2-phenyl-3-(1H-pyrrol-2-yl)acrylonitrile compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

Pharmaceutical compositions useful herein also may comprise solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

3. Delivery to Plants/Crops, Facilities, Habitats

The 2-phenyl-3-(1H-pyrrol-2-yl)acrylonitrile compounds can be readily formulated by art-known methods for delivery for killing, suppressing, and/or inhibiting endo or ectoparasites in and/or on plants generally, and particularly in crop plants, e.g., to kill and/or suppress any of the myriad plant pests enumerated above. In addition, the 2-phenyl-3-(1H-pyrrol-2-yl)acrylonitrile compounds can be applied and/or distributed into selected environmental areas to kill and/or suppress endo or ectoparasites, where desired. These compounds are readily formulated, by methods known to the art, into compositions suitable for such applications. Such compositions optionally include more than one of the inventive compounds, each selected for an optimal spectrum of activity. In certain optional embodiments, the compositions include other agents, e.g., other art-known antiparasitic agents, pesticides and the like, as enumerated supra, that may provide a useful complementary or synergistic anti-parasitical effect.

It is further contemplated that the compositions optionally include other useful agents, including weed killers, fertilizers, and the like, for efficient agriculture management.

Compositions for such distribution include solutions, suspensions and dry forms of the inventive compound(s) as discussed supra. This process of administering such compositions can be achieved by methods well known to the art. These include spraying, brushing, dipping, rinsing, washing, dusting, using art-known equipment, in a selected area. The selected area optionally includes plants, e.g., crops, and/or animals.

Thus, environmental areas contemplated to be treated in this way include, e.g., fields, orchids, gardens and the like, buildings and their environs, including landscaping; storage facilities, transport or fixed storage containers or analogous structures and structural components, such as walls, floors, roofs, fences, windows and window screens, and the like. Animal living spaces are also included, e.g., animal pens, chicken coops, corals, barns and the like. Human homes and other human residential, business or commercial and educational facilities are also contemplated to be treated or contacted with the inventive compounds or compositions thereof as described above.

Application can be achieved using art-known spraying devices, e.g., self-pressurized aerosol containers, larger devices employing compressed air or centrifugal distribution, as well as crop dusters, and the like.

Confirming Anti-Parasite Activity

Exemplified compounds of Formula 1 are listed by Tables 1a and 1b, above. The activity of these compounds against *Haemonchus contortus* and cat fleas (*Ctenocephalides felis*) is summarized by Table 7, below. The data is presented in the following formats.

The $LD_{99}$ value is the dose, expressed as μg/ml, that was required to kill 99% of the sample of *Haemonchus contortus*.

The $LC_{50}$ value is the concentration, expressed as μg/cm², that was required to kill 50% of the sample of cat fleas on contact with the tested compound. Certain tests are also reported as the percent of a sample of cat fleas that were killed at a concentration of 1.26 μg/cm² ("% kill"), for the compounds tested in this way.

TABLE 7

| | Activity | | |
|---|---|---|---|
| N° | $LD_{99}{}^a$ | % Kill | $LC_{50}$ |
| 1 | 0.75 | 28 | |
| 2 | 0.406 | 95 | 0.17 |
| 3 | 3 | 15 | |
| 4 | 0.625 | 20 | |
| 5 | 3 | 6 | |
| 6 | 1.875 | 13 | |
| 7 | 5.5 | 6 | |
| 8 | 5 | 6 | |
| 9 | 0.938 | 56 | 9.94 |
| 10 | 1.625 | 78 | 0.78 |
| 11 | — | 18 | |
| 12 | 3.25 | | |
| 13 | 3 | 8 | |
| 14 | 1.5 | 31 | |
| 15 | 3.25 | 87 | 0.478 |
| 16 | 3.75 | 100 | 0.076 |
| 17 | 0.469 | 98 | 0.259 |
| 18 | 7.5 | 46 | |
| 19 | 6 | 26 | |
| 20 | 10 | 44 | |
| 21 | — | 24 | |
| 22 | 5.5 | 19 | |
| 23 | 0.469 | 23 | |
| 24 | 2.75 | 19 | |
| 25 | 2.5 | 92 | 0.594 |
| 26 | 0.938 | 69 | |
| 27 | 0.406 | 78 | |
| 28 | 2.5 | 19 | 0.295 |
| 29 | 5 | 15 | |
| 30 | 11 | 18 | |
| 31 | 1.75 | 27 | |
| 32 | 0.234 | 42 | |
| 33 | 3 | 15 | |
| 34 | 0.813 | 21 | |
| 35 | — | 21 | |
| 36 | 0.688 | 14 | |
| 37 | — | 11 | |
| 38 | 3.25 | 30 | |
| 39 | 0.938 | 24 | |
| 40 | — | 6 | |
| 41 | 1.75 | 15 | |
| 42 | — | | |
| 43 | — | 6 | |
| 44 | — | | |
| 45 | — | | |
| 46 | — | | |
| 47 | 0.75 | 17 | |
| 48 | 2.5 | 5 | |
| 49 | 14 | | |
| 50 | — | | |
| 51 | 7.5 | | |
| 52 | — | | |
| 53 | — | | |
| 54 | 7 | | |
| 55 | — | 10 | |
| 56 | 6.5 | | |
| 57 | — | | |
| 58 | — | | |
| 59 | — | | |
| 60 | — | 19 | |
| 61 | — | | |
| 62 | 6 | | |
| 63 | 13 | | |
| 64 | — | 20 | |
| 65 | — | | |
| 66 | 2.5 | 28 | |
| 67 | — | 7 | |
| 68 | — | 27 | |
| 69 | 2.5 | 5 | |
| 70 | 7.5 | 17 | |
| 71 | 3.25 | 10 | |
| 72 | 1.25 | 42 | |
| 73 | 0.469 | 7 | |
| 74 | 3 | 30 | |
| 75 | 0.875 | 58 | |
| 76 | 0.375 | 12 | |
| 77 | 14 | 3 | |
| 78 | 3.5 | 8 | |
| 79 | 3.75 | 9 | |
| 80 | — | | |
| 81 | 1.25 | 5 | |
| 82 | 1.25 | 6 | |
| 83 | 12 | | |
| 84 | 10 | 19 | |
| 85 | 1.25 | 16 | |
| 86 | 5.5 | 20 | |
| 87 | — | 100 | |
| 88 | — | 44 | |
| 89 | — | 2 | |
| 90 | — | 14 | |
| 91 | — | 9 | |

$^a$the symbol '—' indicates tested but inactive up to 15 μg/ml

EXAMPLES

The following preparative examples of preferred novel derivatives of Formula 1 serve to provide further appreciation of the invention but are not meant in any way to restrict the effective scope of the invention.

Example 1

Preparation of Reagents

It should be noted that the compounds of Tables 1a and 1b, supra (also listed by Table 8, infra) where prepared using commercially available reagents, when available. Those substituted phenyl acetonitriles that were not available commercially were prepared from available benzoic acids, benzaldehydes, benzyl alcohols or benzyl halides by the well established procedures given in J. March, "ADVANCED ORGANIC CHEMISTRY", Third Edition, John Wiley & Sons, New York, 1985, incorporated by reference herein in its entirety.

In addition, 4-bromo-1H-pyrrole-2-carbaldehyde was prepared according to C. Jaureguiberry, et al. *Acad. Sc. Paris*, 1971, 273, 276, incorporated by reference herein in its entirety, and used to prepare Compounds 11, 12, 23, and 29-31, and 34, as listed by Tables 1a and 8.

4,5-dichloro-1H-pyrrole-2-carbaldehyde was prepared according to P. E. Sonnet, *J. Org. Chem.*, 1972, 37, 925, incorporated by reference herein in its entirety, and used to prepare Compound 3 as listed by Tables 1a and 8, according to the following Examples.

1-ethoxymethyl-1H-pyrrole-2-carbaldehyde was prepared from 1H-pyrrole-2-carbaldehyde and sodium hydride followed by treatment with chloromethylethyl ether, and used to prepare Compounds 7, 8 and 49-65, as listed by Tables 1a, 1b and 8, according to the following Examples.

1-(diethoxymethyl)-1H-pyrrole-2-carbaldehyde was prepared as indicated in M. Bergauer, P. Gmeiner, *Synthesis*, 2001, (15), 2281, incorporated by reference herein in its entirety, and used to prepare Compounds 41-46, as listed by Tables 1a and 8, according to the following Examples.

Example 2

Preparation of (Z)-2-(4-Chloro-phenyl)-3-(1H-pyrrol-2-yl)acrylonitrile

This compound was prepared using Triton B as phase transfer catalyst, as follows.

A suspension of 1H-pyrrole-2-carbaldehyde (3.3 g, 34.7 mmol) and 4-chlorophenylacetonitrile (5.5 g, 33.0 mmol, 0.95 equivalents) in water (50 ml) was heated to 50° C. When all the solid material had melted, the vigorously stirred mixture was treated with 40% aqueous Triton B (14 ml, 5.6 mmol). Precipitation began almost immediately. Stirring was continued for 5 h at 50° C., breaking up lumps when necessary. The still warm suspension was filtered through a sintered glass funnel and washed with warm water. The yellow precipitate was dried at the pump (6.63 g). This is Compound 2 in TABLE 8.

Example 3

Preparation of (Z)-2-(4-Chloro-phenyl)-3-(1-methyl-1H-pyrrol-2-yl)acrylonitrile

A suspension of 4-chlorophenylacetonitrile (500 mg, 3.30 mmol) and 1-methyl-1H-pyrrole-2-carbaldehyde (370 mg, 3.39 mmol, 1.03 equiv.) in water (5 ml) was treated with 40% aqueous Triton B (1.4 ml, 3.3 mmol). Precipitate began forming almost immediately. After stirring for 2 h, the precipitate was filtered off, washed with water, and dried to afford a yellow solid (682 mg). This is Compound 6 in Table 8.

Example 4

Preparation of (Z)-2-(4-Chloro-phenyl)-3-(1-ethoxymethyl-1H-pyrrol-2-yl)acrylonitrile To a solution of 4-chlorophenylacetonitrile (500 mg, 3.30 mmol), 1-ethoxymethyl-1H-pyrrole-2-carbaldehyde (520 mg, 3.39 mmol, 1.03 equiv.), and 18-crown-6 ether as a phase transfer catalyst (87 mg, 0.33 mmol) in toluene (30 ml) was added potassium hydroxide (185 mg, 3.30 mmol) and the mixture was heated to 80° C. for 3 h, then stirred at room temperature overnight. The solution was filtered through a small plug of silica and concentrated to afford an oil (705 mg). This is Compound 7 in Table 8.

Example 5

Preparation of (Z)-2-(2-Methyl-phenyl)-3-(1H-pyrrol-2-yl)acrylonitrile Under High Pressure A thick walled tube was charged with 1H-pyrrole-2-carbaldehyde (2.0 g, 21.0 mmol), 2-methylphenylacetonitrile (2.5 g, 18.9 mmol, 0.9 equivalents), ethanol (75 ml), and 40% aqueous Triton B (4.0 ml, 3.3 mmol). The tube was sealed and heated to 90° C. for 4 days. Removal of the solvent, followed by chromatography on silica gel using dichloromethane/petroleum spirits (20:80) as eluant afforded a yellow solid (1.2 g). This is Compound 16 in Table 8.

Example 6

Preparation of (Z)-2-(4-chlorophenyl)-3-(1-(3-methylbut-2-enyl)-1H-pyrrol-2-yl)acrylonitrile This compound was prepared with a subsequent modification of $R_1$, as follows.

A solution of (Z)-2-(4-Chloro-phenyl)-3-(1H-pyrrol-2-yl) acrylonitrile being Compound 2 in Table 8 (200 mg, 0.875 mmol) in dry acetone (35 ml) was treated with $K_2CO_3$ (121 mg) followed by dimethylallyl bromide (111 µl, 0.962 mmol, 1.1 equivalents). The mixture was heated to a gentle reflux for 20 h. The reaction was cooled to room temperature and filtered. The filtrate was chromatographed on silica gel using ethylacetate/petroleum spirits (1:1) as eluant to afford the title compound as a yellow oil (85 mg). This is Compound 80 in Table 8.

Example 7

Preparation of (Z)-2-(4-Chlorophenyl)-3-(1-propanoyl-1H-pyrrol-2-yl)acrylonitrile To a stirred solution (Z)-2-(4-chlorophenyl)-3-(1-methyl-1H-pyrrol-2-yl)acrylonitrile (this is compound 2 in Table 8) (600 mg, 2.62 mmol), triethylamine (320 mg), and 4-dimethylaminopyridine (32 mg) in dichloromethane (20 mL) was added propionic anhydride (375 mg). The mixture was stirred at room temperature for 7 h. Triethylamine (320 mg) and propionic anhydride (375 mg) was added and the mixture stirred at room temperature for 48 h. The reaction mixture was poured into ether (200 mL) and the ether was washed with 10% aqueous citric acid solution (50 mL, water (2×50 mL) and saturated brine (50 mL). The ether layer was collected, dried over magnesium sulfate, filtered and evaporated. The residue was recrystallized from ether/light petroleum to afford the title compound as yellow needles (611 mg). This is Compound 76 in Table 8.

Example 8

Analytic Data For Prepared Compounds

Table 8 below provides analytic data for compounds of Formula 1 that are listed in Tables 1a and 1b, above, using both nmr and mass spectroscopy.

TABLE 8

| N° | m/z | $^1$H-nmr - major isomer | mp(° C.) | Lit. Ref. |
|---|---|---|---|---|
| 1 | | 9.80(brs, 1H), 7.55(t, J 1.8Hz, 1H), 7.44(t, J 1.8Hz, 1H), 7.40(s, 1H), 7.34(s, 1H), 7.28-7.33(m, 2H), 7.09(m, 1H), 6.74(m, 1H), 6.35(m, 1H) | | |

TABLE 8-continued

| N° | m/z | ¹H-nmr - major isomer | mp(° C.) | Lit. Ref. |
|---|---|---|---|---|
| 2 | [A]APCI− 227.2(M−1) | 9.78(brs, 1H), 7.51(d, J 8.8Hz, 2H), 7.38(d, J 8.8Hz, 2H), 7.37(s, 1H), 7.09(m, 1H), 6.70(m, 1H), 6.36(m, 1H) | Lit 122-123 | 1 |
| 3 | [B]ESI− 295.0(M−1) | | | |
| 4 | APCI− 261.2(M−1) | 9.83(brs, 1H), 7.67(m 4H), 7.12(m, 1H), 6.76(m, 1H), 6.38(m, 1H) | | 2 |
| 5 | | | | 3 |
| 6 | | | Lit 184-185 | 1 |
| 7 | APCI+ 287.2(M+1) | 7.60(s, 1H), 7.56(m, 1H), 7.55(d, J 8.8Hz, 2H), 7.38(d, J 8.8Hz, 2H), 6.93(m, 1H), 6.33(m, 1H), 5.39(s, 2H), 3.44(q, J 6.9Hz, 1H), 1.18(t, J 6.9Hz, 1H) | | |
| 8 | APCI− 320.2(M−) | 7.70(d, J 8.4Hz, 2H), 7.62(d, J 8.4Hz, 2H), 7.43(s, 1H), 6.85(dd, J 2.6 and 1.5Hz, 1H), 6.02(dd, J 4.0 and 2.9Hz, 1H), 5.93(dm, J 4.4Hz, 1H), 5.33(s, 2H), 3.45(d, J 6.9Hz, 3H), 1.21(t, J 6.9Hz, 3H); ¹⁹F{¹H} −63.25(s, 3F) | | |
| 9 | ESI− 261.0(M−1) | 9.81(brs, 1H), 7.68-7.84(m, 2H), 7.51-7.62(m, 2H), 7.46(s, 1H), 7.11(m, 1H), 6.76(m, 1H), 6.38(m, 1H); ¹⁹F{¹H} −63.29(s, 3F) | | 2 |
| 10 | | 9.80(brs, 1H), 7.40(s, 1H), 7.36(m, 2H), 7.27(dm, J 10.2Hz, 1H), 7.09(m, 1H), 7.01(m, 1H), 6.73(m, 1H), 6.37(m, 1H); ¹⁹F{¹H} −112.41(s, 1F) | | |
| 11 | | 9.79(brs, 1H), 7.67(s, 4H), 7.37(s, 1H), 7.06(dd, J 2.9 and 1.6Hz, 1H), 6.77(dd, J 2.7 and 1.6Hz, 1H); ¹⁹F{¹H} −63.18(s, 3F) | | |
| 12 | | 9.74(brs, 1H), 7.71-7.82(m, 2H), 7.53-7.61(m, 2H), 7.35(s, 1H), 7.07(dd, J 2.9 and 1.5Hz, 1H), 6.76(dd, J 2.9 and 1.5Hz, 1H); ¹⁹F{¹H} −63.30(s, 3F) | | |
| 13 | | 9.84(brs, 1H), 7.48(d, J 1.5Hz, 1H), 7.30-7.40(m, 2H), 7.17(s, 1H), 7.11(m, 1H), 6.69(m, 1H), 6.37(m, 1H) | | |
| 14 | | 9.73(brs, 1H), 7.50(d, J 9.5Hz, 2H), 7.28(s, 1H), 7.03(m, 1H), 6.93(d, J 9.5Hz, 2H), 6.64(m, 1H), 6.33(m, 1H), 3.84(s, 3H) | Lit 118-119 | 1 |
| 15 | | 7.52(d, J 8.8Hz, 2H), 7.43(d, J 8.8Hz, 2H), 7.37(s, 1H), 7.06(m, 1H), 6.67(m, 1H), 6.34(m, 1H), 1.34(s, 9H) | | |
| 16 | | 9.81(brs, 1H), 7.18-7.30(m, 4H), 7.07(m, 1H), 7.03(s, 1H), 6.63(m, 1H), 6.34(m, 1H), 2.48(s, 3H) | | |
| 17 | | 9.80(brs, 1H), 7.53-7.63(m, 2H), 7.27-7.47(m, 4H), 7.07(m, 1H), 6.69(m, 1H), 6.35(m, 1H) | Lit 98-99 | 1 |
| 18 | | 9.81(brs, 1H), 7.57-7.69(m, 6H), 7.30-7.53(m 4H), 7.08(m, 1H), 6.71(m, 1H), 6.37(m, 1H) | | |
| 19 | | 9.72(brs, 1H), 7.24(s, 1H), 7.00-7.11(m, 3H), 6.84(d, J 8.0Hz, 1H), 6.64(m, 1H), 6.33(m, 1H), 6.00(s, 2H) | | |
| 20 | | 7.68(s, 4H), 7.50(s, 1H), 7.14(dd, J 2.6 and 1.5Hz, 1H), 6.80(dd, J 3.7 and 1.5Hz, 1H), 6.39(dd, J 3.7 and 2.6Hz, 1H) | | |
| 21 | | 7.71(d, J 8.9Hz, 2H), 7.64(d, J 8.9Hz, 2H), 7.55(dm, J 4.4Hz, 1H), 7.43(s, 1H), 6.87(m, 1H), 6.33(dd, J 4.4 and 2.6Hz, 1H), 3.76(s, 3H) | | 2 |
| 22 | | 7.81(s, 1H), 7.77(m, 1H), 7.47-7.62(m, 3H), 7.39(s, 1H), 6.86(m, 1H), 6.33(dd, J 4.0 and 2.5, 1H), 3.77(s, 3H) | | |
| 23 | | 9.70(brs, 1H), 7.50(d, J 8.8Hz, 2H), 7.38(d, J 8.8Hz, 2H), 7.29(s, 1H), 7.03(dd, J 2.9 and 1.5Hz, 1H), 6.69(dd, J 2.9 and 1.6Hz, 1H) | | |
| 24 | | 9.86(brs, 1H), 7.27-7.48(m, 4H), 7.18(s, 1H), 7.09(m, 1H), 6.67(m, 1H), 6.35(m, 1H) | | |
| 25 | | 9.83(brs, 1H), 7.52(dt, J 7.7 and 1.8Hz, 1H), 7.50(s, 1H), 7.05-7.38(m, 4H), 6.71(m, 1H), 6.36(m, 1H) | | |

TABLE 8-continued

| N° | m/z | ¹H-nmr - major isomer | mp(° C.) | Lit. Ref. |
|---|---|---|---|---|
| 26 | | 9.78(brs, 1H), 7.47(d, J 8.4Hz, 2H), 7.36(s, 1H), 7.21(d, J 8.4Hz, 2H), 7.04(m, 1H), 6.67(m, 1H), 6.34(m, 1H), 2.38(s, 3H) | Lit 104-105 | 1 |
| 27 | | 9.76(brs, 1H), 7.64(d, J 2.2Hz, 1H), 7.47(d, J 8.8Hz, 1H), 7.38(dd, J 8.8 and 2.2Hz, 1H), 7.37(s, 1H), 7.10(m, 1H), 6.74(m, 1H), 6.37(m, 1H) | | |
| 28 | | 9.76(brs, 1H), 7.48-7.60(m, 2H), 7.32(s, 1H), 7.03-7.18(m, 3H), 6.68(m, 1H), 6.35(m, 1H) | | |
| 29 | | 9.68(brs, 1H), 7.64(d, J 2.2Hz, 1H), 7.49(d, J 8.4Hz, 1H), 7.38(dd, J 8.4 and 2.2Hz, 1H), 7.27(s, 1H), 7.06(dd, J 2.9 and 1.5Hz, 1H), 6.72(dd, J 2.9 and 1.7Hz, 1H) | | |
| 30 | | 9.67(brs, 1H), 7.54(dd, J 8.8 and 5.1Hz, 2H), 7.21(s, 1H), 7.11(dd, J 8.8 and 8.8Hz, 2H), 7.02(dd, J 2.9 and 1.5Hz, 1H), 6.67(m, 1H) | | |
| 31 | | 9.70(brs, 1H), 7.32-7.43(m, 2H), 7.29(s, 1H), 7.26(dm, J 9.5Hz, 1H), 7.04(m, 2H), 6.71(m, 1H) | | |
| 32 | | 9.89(brs, 1H), 8.16-8.25(m, 1H), 7.82-7.96(m, 3H), 7.44-7.66(m, 4H), 7.22(s, 1H), 7.11(m, 1H), 6.68(m, 1H), 6.38(m, 1H) | | |
| 33 | | 7.52(d, J 8.7Hz, 2H), 7.42(d, J 8.7Hz, 2H), 7.38(s, 1H), 7.08(s, 1H), 6.71(s, 1H), 6.36(m, 1H) | | |
| 34 | | 9.80(brs, 1H), 8.00-8.23(m, 1H), 7.76-7.98(m, 3H), 7.38-7.70(m, 4H), 7.12(s, 1H), 7.06(m, 1H), 6.69(m, 1H) | | |
| 35 | | 9.86(brs, 1H), 7.49(dd, J 7.3 and 2.2Hz, 1H), 7.19-7.35(m, 2H), 7.15(s, 1H), 7.11(m, 1H), 6.69(m, 1H), 6.37(m, 1H) | | |
| 36 | | 9.78(brs, 1H), 7.73(d, J 8.8Hz, 2H), 7.40(s, 1H), 7.31(d, J 8.8Hz, 2H), 7.09(m, 1H), 6.71(m, 1H), 6.36(m, 1H) | | |
| 37 | | 9.81(brs, 1H), 7.75(dm, J 7.3Hz, 1H), 7.60-7.68(m, 2H), 7.55(s, 1H), 7.38-7.49(m, 1H), 7.14(m, 1H), 6.83(m, 1H), 6.39(m, 1H) | | |
| 38 | | 9.85(brs, 1H), 7.65(d, J 8.8Hz, 1H), 7.38(m, 2H), 7.23(m, 1H), 7.12(s, 1H), 7.10(m, 1H), 6.67(m, 1H), 6.36(m, 1H) | | |
| 39 | | 9.79(brs, 1H), 7.71(dd, J 1.8 and 1.8Hz, 1H), 7.50(dm, J 7.7Hz, 1H), 7.44(dm, J 7.7Hz, 1H), 7.39(s, 1H), 7.27(dd, J 7.7 and 7.7Hz, 1H), 7.10(m, 1H), 6.73(m, 1H), 6.37(m, 1H) | | |
| 40 | | 9.87(brs, 1H), 8.27(d, J 8.8Hz, 2H), 7.72(d, J 8.8Hz, 2H), 7.55(m, 1H), 7.17(m, 1H), 6.83(m, 1H), 6.41(m, 1H) | Lit 206-207 | 1 |
| 41 | | 7.90(s, 1H), 7.55(m, 1H), 7.53(d, J 8.8Hz, 1H), 7.37(d, J 8.8Hz, 1H), 7.09(dd, J 2.9 and 1.8Hz, 1H), 6.31(dd, J 3.7 and 2.9Hz, 1H), 6.06(s, 1H), 3.56(m, 4H), 1.23(t, J 7.3Hz, 6H) | | |
| 42 | | 8.07(s, 1H), 7.68(s, 4H), 7.64(m, 1H), 7.14(m, 1H), 6.34(m, 1H), 6.07(s, 1H), 3.57(m, 4H), 1.23(t, J 7.3Hz, 6H) | | |
| 43 | | 7.96(s, 1H), 7.60(m, 1H), 7.54(m, 1H), 7.05-7.37(m, 4H), 6.32(m, 1H), 6.05(s, 1H), 3.56(m, 4H), 1.23(t, J 7.3Hz, 6H) | | |
| 44 | | 8.26(d, J 8.8Hz, 2H), 8.14(s, 1H), 7.74(d, J 8.8Hz, 2H), 7.68(m, 1H), 7.16(m, 1H), 6.36(m, 1H), 6.09(s, 1H), 3.58(m, 4H), 1.24(t, J 7.3Hz, 6H) | | |
| 45 | | 7.91(s, 1H), 7.57(m, 2H), 7.48(dm, J 7.3Hz, 1H), 7.25-7.40(m, 2H), 7.11(m, 1H), 6.32(m, 1H), 6.07(s, 1H), 3.57(m, 4H), 1.24(t, J 7.3Hz, 6H) | | |
| 46 | | 7.93(s, 1H), 7.58(m, 1H), 7.24-7.44(m, 3H), 7.10(m, 1H), 6.94-7.07(m, 1H), 6.32(m, 1H), 6.07(s, 1H), 3.57(m, 4H), 1.24(t, J 7.3Hz, 6H) | | |

TABLE 8-continued

| N° | m/z | ¹H-nmr - major isomer | mp(° C.) | Lit. Ref. |
|---|---|---|---|---|
| 47 | | 9.75(brs, 1H), 7.37(ddd, J 11.4, 7.3 and 2.2Hz, 1H), 7.31(s, 1H), 7.30(m, 1H), 7.19(dd, J 9.5 and 8.5Hz, 1H), 7.09(s, 1H), 6.72(s, 1H), 6.36(m, 1H); 19F{1H} −136.53(d, J 21.5Hz, 1F), −138.05(d, J 21.5Hz, 1F) | 131-132 | |
| 48 | | 9.81(brs, 1H), 7.47(s, 1H), 7.45(dd, J 8.8 and 8.4Hz, 1H), 7.13-7.23(m, 2H), 7.10(m, 1H), 6.72(m, 1H), 6.36(m, 1H) | | |
| 49 | | 7.50-7.62(m, 4H), 7.11(dd, J 4.4 and 4.4Hz, 2H), 6.91(dd, J 2.5 and 1.5Hz, 1H), 6.33(ddm, J 4.0 and 2.6Hz, 1H), 5.38(s, 2H), 3.42(q, J 6.9Hz, 2H), 1.18(t, J 6.9Hz, 3H); $^{19}F\{^{1}H\}$ −113.59(s, 1F) | | |
| 50 | | 7.88(s, 1H), 7.40-7.80(m, 5H), 6.99(m, 1H), 6.36(dd, J 3.8 and 2.9Hz, 1H), 5.36(s, 2H), 3.43(q, J 6.9Hz, 2H), 1.17(t, J 6.9Hz, 3H) | | |
| 51 | | 7.62(s, 1H), 7.55(m, 1H), 7.53(d, J 8.8Hz, 2H), 7.46(d, J 8.8Hz, 2H), 6.92(m, 1H), 6.33(dd, J 4.4 and 2.9Hz, 1H), 5.38(s, 2H), 3.42(q, J 7.0Hz, 2H), 1.18(t, J 7.0Hz, 3H) | | |
| 52 | | 7.64(brd, J 4.0Hz, 1H), 7.13-7.49(m, 4H), 6.94(dd, J 2.4 and 1.5Hz, 1H), 6.36(dd, J 3.7 and 2.4Hz, 1H), 5.32(s, 2H), 3.42(q, J 7.0Hz, 2H), 1.14(t, J 7.0Hz, 3H) | | |
| 53 | | 8.09(m, 1H), 7.45-7.95(m, 8H), 6.94(dd, J 2.3 and 1.5Hz, 1H), 6.35(dd, J 4.4 and 2.3Hz, 1H), 5.43(s, 2H), 3.46(q, J 7.1Hz, 2H), 1.21(t, J 7.1Hz, 3H) | | |
| 54 | | 8.19(m, 1H), 7.60(brd, J 4.4Hz, 1H), 7.10-7.57(m, 4H), 6.93(m, 1H), 6.34(dd, J 4.4 and 2.9Hz, 1H), 1.24(s, 2H), 3.42(q, J 7.1Hz, 1H), 1.17(t, J 7.1Hz, 1H) | | |
| 55 | | 7.74(s, 1H), 7.01-7.61(m, 5H), 7.94(dd, J 2.9 and 1.5Hz, 1H), 7.34(dd, J 4.4 and 2.9Hz, 1H), 5.35(s, 2H), 3.45(q, J 7.0Hz, 2H), 1.18(t, J &.0Hz, 3H); $^{19}F\{^{1}H\}$ −117.72(s, $^{1}F$) | | |
| 56 | | 7.67(d, J 1.7Hz, 1H), 7.60(s, 1H), 7.57(brd, J 4.0Hz, 1H), 7.46(s, 1H), 7.44(d, J 1.7Hz, 1H), 6.95(dd, J 2.7 and 1.6Hz, 1H), 6.34(dd, J 3.7 and 2.7Hz, 1H), 5.40(s, 2H), 3.43(q, J 7.0Hz, 2H), 1.19(t, J 7.0Hz, 3H) | | |
| 57 | | 7.40-7.80(m, 5H), 7.22(s, 1H), 6.92(s, 1H), 6.34(dd, J 3.7 and 2.2Hz, 1H), 5.29(s, 2H), 3.39(q, J 7.0Hz, 2H), 1.13(t, J 7.0Hz, 3H); $^{19}F\{H\}$ −61.31(3F) | | |
| 58 | | 7.74(m, 1H), 7.61(s, 1H), 7.40-7.60(m, 3H), 7.28(t, J 8.0Hz, 1H), 6.93(t, J 1.8Hz, 1H), 6.34(dd, J 3.3 and 2.9Hz, 1H), 5.39(s, 2H), 3.43(q, J 7.0Hz, 2H), 1.19(t, J 7.0Hz, 3H) | | |
| 59 | | 7.99(s, 2H), 7.82(s, 1H), 7.74(s, 1H), 7.65(dd, J 4.4 and 2.9Hz, 1H), 6.99(dd, J 2.9 and 1.5Hz, 1H), 6.37(dd, J 4.4 and 2.9Hz, 1H), 5.43(s, 2H), 3.45(q, J 7.0Hz, 2H), 1.20(t, J 7.0Hz, 3H); $^{19}F\{^{1}H\}$ −63.50(6F) | | |
| 60 | | {$^{19}F$} 7.65(s, 1H), 7.58(d, J 3.7Hz, 1H), 7.53(d, J 8.8Hz, 2H), 6.94(m, 2H), 6.90(d, J 2.6Hz, 1H), 6.34(m, 1H), 5.35(s, 2H), 3.43(q, J 7.0Hz, 2H), 1.17(t, J 7.0Hz, 3H); $^{19}F\{^{1}H\}$ −109.52(d, J 8.5Hz, 1F), −113.11(d, J 8.5Hz, 1F) | | |
| 61 | | {$^{19}F$} 7.65(d, J 3.3Hz, 1H), 7.43(s, 1H), 7.30(t, J 8.4Hz, 1H), 6.97(d, J 8.4Hz, 2H), 6.94(m, 1H), 6.35(m 1H), 5.33(s, 2H), 3.41(q, J 7.0Hz, 2H), 1.16(q, J 7.0Hz, 2H); $^{19}F\{^{1}H\}$ −112.43(s, 1F) | | |
| 62 | | {$^{19}F$} 7.55(s, 2H), 7.40(s, 1H), 7.34(dd, J 8.7 and 2.2Hz, 1H), 7.20(d, J 8.7Hz, 1H), 6.93(s, 1H), 6.33(m, 1H), 5.39(s, 2H), 3.44(d, J 6.9Hz, 2H), 1.18(t, J 6.9Hz, | | |

TABLE 8-continued

| N° | m/z | ¹H-nmr - major isomer | mp(° C.) | Lit. Ref. |
|---|---|---|---|---|
| | | 3H); ¹⁹F{¹H} −136.70(d, J 22.0Hz, 1F), −138.01(d, J 22.0Hz, 1F) | | |
| 63 | | 7.61(s, 1H), 7.53(brd, J 3.7Hz, 1H), 7.43(m, 2H), 7.33(d, J 8.0Hz, 1H), 7.13(br d, J 7.3Hz, 1H), 6.92(m, 1H), 6.33(dd, J 4.4 and 2.9Hz, 1H), 5.39(s, 2H), 3.43(q, J 7.0Hz, 2H), 2.41(s, 3H), 1.19(t, J 7.0Hz, 3H) | | |
| 64 | | 7.59(s, 1H), 7.46-7.56(m, 3H), 7.22(d, J 7.7Hz, 2H), 6.90(dd, J 2.7 and 1.5Hz, 1H), 6.32(dd, J 3.7 and 2.7Hz, 1H), 5.37(s, 2H), 3.44(q, J 7.1Hz. 2H), 2.38(s, 3H), 1.18(t, J 7.1Hz, 3H) | | |
| 65 | | 7.59(s, 1H), 7.55(d, J 4.4Hz, 1H), 7.25-7.45(m, 4H), 7.90-7.20(m, 4H), 6.33(dd, J 4.4 and 2.9Hz, 1H), 5.36(s, 2H), 3.41(q, J 7.1Hz. 2H), 1.15(t, J 7.1Hz, 3H) | | |
| 66 | | 9.85(brs, 1H), 8.04(s, 1H), 7.80-7.90(m, 4H), 7.45-7.60(m, 3H), 7.09(m, 1H), 6.74(s, 1H), 6.37(m, 1H) | | |
| 67 | | 9.86(brs, 1H), 7.97(m, 1H), 7.25-7.35(m, 2H), 7.04-7.15(m, 2H), 6.69(s, 1H), 6.36(m, 1H); ¹⁹F{¹H} −110.30(s, 1F) | | |
| 68 | | 9.83(brs, 1H), 7.97(s, 2H), 7.80(s, 1H), 7.52(s, 1H), 7.16(m, 1H), 6.85(m, 1H), 6.41(m, 1H); ¹⁹F{¹H} −63.51(s, 6F) | | |
| 69 | | {¹⁹F} mix E/Z 9.80(brs, 1H), 8.01(d, J 9.1Hz, 1H), 7.87(d, J 2.2Hz, 1H), 7.82(s, 1H), 7.60(d, J 2.6Hz, 1H), 7.48(d, J 9.1Hz, 1H), 7.41(s, 1H), 7.21(dd, J 9.1 and 2.6Hz, 1H), 7.09(m, 1H), 6.96(d, J 2.6Hz, 1H), 6.94(m, 1H), 6.90(d, J 2.6Hz, 1H), 6.84(dd, J 4.0 and 0.7Hz, 1H), 6.70(m, 1H), 6.36(m, 1H); ¹⁹F{¹H} −109.69(d, J 9.2Hz, 1F), −110.79(d, J 9.2Hz, 1F) | 117-119 | |
| 70 | | {¹⁹F} mix E/Z 9.88(brs, 1H), 7.96(d, J 2.2Hz, 1H), 7.89(s, 1H), 7.72(d, J 8.1Hz, 1H), 7.56(t, J 8.1Hz, 1H), 7.30(t, J 8.1Hz, 1H), 7.23(s, 1H), 7.15(d, J 8.1Hz, 1H), 7.11(m, 1H), 6.98(d, J 8.8Hz, 2H), 6.94(dd, J 4.0 and 2.9Hz, 1H), 6.86(dd, J 4.0 and 0.7Hz, 1H), 6.70(m, 1H), 6.36(m, 1H); ¹⁹F{¹H} −112.42(s, 2F) | decomp. | |
| 71 | ESI− 285.0 (M−1) | 9.78(brs, 1H), 7.30-7.40(m, 5H), 7.24(m, 1H), 7.14(tm, J 7.7Hz, 1H), 7.01-7.08(m, 3H), 6.93(dm, J 7.7Hz, 1H), 6.69(m, 1H), 6.35(m, 1H) | | |
| 72 | | 9.79(brs, 1H), 7.39(s, 2H), 7.37(obsc d, J 7.7Hz, 1H), 7.30(t, J 7.7Hz, 1H), 7.13(d, J 7.7Hz, 1H), 7.06(s, 1H), 6.68(s, 1H), 6.35(m, 1H), 2.40(s, 3H) | | |
| 73 | | 9.74(brs, 1H), 7.75(dd, J 6.2 and 2.2Hz, 1H), 7.48(ddd, J 8.8, 4.4 and 2.6Hz, 1H), 7.32(s, 1H), 7.16(dd, J 8.8 and 8.0Hz, 1H), 7.09(m, 1H), 6.72(m, 1H), 6.37(m, 1H) | | |
| 74 | | 9.84(brs, 1H), 7.38(dd, J 8.6 and 6.0Hz, 1H), 7.21(dd, J 8.4 and 2.6Hz, 1H), 7.12(s, 1H), 6.98-7.11(m, 2H), 6.67(m, 1H), 6.36(m, 1H) | | |
| 75 | | 9.78(brs, 1H), 7.51(d, J 8.4Hz, 2H), 7.37(s, 1H), 7.25(d, J 8.4Hz, 2H), 7.06(m, 1H), 6.67(m, 1H), 6.34(m, 1H), 2.68(q, J 7.7Hz, 2H), 1.26(t, J 7.7Hz, 3H) | | |
| 76 | | 8.48(s, 1H), 7.59(d, J 8.8Hz, 2H), 7.47(d, J 4.4Hz, 1H), 7.38(d, J 8.8Hz, 2H), 7.32(dd, J 3.7 and 1.5Hz, 1H), 6.43(t, J 3.7Hz, 1H), 2.97(q, J 7.3Hz, 2H), 1.31(t, J 7.3Hz, 3H) | | |
| 77 | ESI+ 319.0(M+1) | 7.59(d, J 3.1Hz, 1H), 7.28-7.40(m, 7H), 7.24(s, 1H), 7.10(s, 1H), 7.08(s, 1H), 6.98(s, 1H), 6.41(t, J 3.0Hz, 1H), 5.25(s, 2H) | | 4 |
| 78 | ESI+ 328.0(M+1), 350.0(M+Na) | 7.45-7.56(m, 4H), 7.31-7.41(m, 2H), 7.00(m, 1H), 6.40(m, 1H), 3.35(q, J 7.1Hz, 4H), 1.22(t, J 7.1Hz, 6H) | | 5 |

TABLE 8-continued

| N° | m/z | ¹H-nmr - major isomer | mp(° C.) | Lit. Ref. |
|---|---|---|---|---|
| 79 | | 8.44(s, 1H), 7.58(d, J 8.1Hz, 1H), 7.49(s, 1H), 7.42(s, 1H), 7.37(d, J 8.1Hz, 1H), 6.34(t, J 1.6Hz, 1H), 1.62(s, 9H) | 128-129 | 6 |
| 80 | EI 296(M⁺) | 7.47-7.50(m, 3H), 7.32-7.41(m, 2H), 6.88(s, 1H), 6.31(s, 1H), 5.30(t, J 6.2Hz, 1H), 4.62(s, 1H), 4.60(s, 1H), 1.79(s, 3H), 1.78(s, 3H) | | 7 |
| 81 | | 9.75(brs, 1H), 7.60(dd, J 6.8Hz and 2.6Hz, 1H), 7.43(ddd, J 8.8, 4.4 and 2.6Hz, 1H), 7.32(s, 1H), 7.18(dd, J 8.8 and 8.6Hz, 1H), 7.09(m, 1H), 6.72(m, 1H), 6.37(m, 1H) | | |
| 82 | ESI+ 333.0(M+1) | 8.20(s, 1H), 7.77(d, J 7.8Hz, 2H), 7.66(m, 2H), 7.50-7.60(m, 4H), 7.36(d, J 8.3Hz, 2H), 7.09(s, 1H), 6.42(s, 1H) | 118-121 | 8 |
| 83 | APCI− 381.1(M−1) | 8.17(s, 1H), 7.62(d, J 8.0Hz, 2H), 7.50-7.60(m, 3H), 7.48(d, J 3.3Hz, 1H), 7.42(d, J 8.4Hz, 2H). 7.28(d, J 8.0Hz, 2H), 6.45(t, J 3.4Hz, 1H), 2.40(s, 3H) | | |
| 84 | APCI− 314.1(M−1) | 7.45-7.55(m, 4H), 7.35-7.45(m, 2H), 6.99(s, 1H), 6.44(s, 1H), 3.56(s, 3H), 2.97(s, 3H) | | |
| 85 | EI 286(M⁺) | 8.45(s, 1H), 7.58(d, J 8.1Hz, 2H), 7.53(s, 1H), 7.46(s, 1H), 7.38(d, J 8.1Hz, 2H), 6.38(s, 1H), 4.00(s, 3H) | 126-127.5 | |
| 86 | EI 362.1(M⁺) | 8.39(s, 1H), 7.40-7.55(m, 9H), 7.34(d, J 7.7Hz, 2H), 6.38(s, 1H), 5.40(s, 2H) | 116-118 | |
| 87 | | 9.78(brs, 1H), 7.50(d, J 8.0Hz, 2H), 7.37(s, 1H), 7.29(d, J 8.0Hz, 2H), 7.05(m, 1H), 6.67(m, 1H), 6.34(m, 1H), 2.94(hept, J 6.9Hz, 1H), 1.27(d, J 6.9Hz, 6H) | 76-78 | |
| 88 | | 7.65(brs, 1H), 7.22(d, J 7.9Hz, 1H), 7.18(s, 2H), 7.13(d, J 7.9Hz, 1H), 6.66(m, 1H), 6.38(m, 1H), 6.16(m, 1H), 2.40(s, 3H), 2.29(s, 3H) | | |
| 89 | | 9.65(brs, 1H), 7.35-7.50(m, 9H), 6.99(m, 1H), 6.97(m, 1H), 6.50(m, 1H), 6.29(m, 1H) | | |
| 90 | | 9.78(brs, 1H), 7.60(t, J 7.6Hz, 1H), 7.52(t, J 7.6Hz, 1H), 7.47(d, J 7.6Hz, 1H), 7.09(s, 1H), 7.01(s, 1H), 6.65(m, 1H), 6.35(m, 1H); ¹⁹F{¹H} −58.53(s, 3F) | | |
| 91 | | 9.89(brs, 1H), 7.39(s, 1H), 7.38(dd, J 7.6 and 1.5Hz, 1H), 7.32(ddd, J 8.4, 7.6 and 1.5Hz, 1H), 7.04(m, 1H), 7.00(td, J 7.6 and 1.1Hz, 1H), 6.95(d, J 8.4Hz, 1H), 6.62(m, 1H), 6.32(m, 1H), 3.92(s, 3H) | | |

[A]"APCI" indicates mass spectroscopy by atmospheric pressure chemical ionization.
[B]"ESI" indicates mass spectroscopy by electrospray ionization.
1) G Alberghina, et al., J. Heterocycl. Chem., 1986, 23, 1747;
2) JP 05100264;
3) CAS Registry Number [675857-75-7];
4) Compound 2 was modified by the procedure of Watanabe et al., Chem. Pharm. Bull., 1191, 39, 1152 to give Compound 77;
5) Compound 2 was modified by the procedure of Castells, et al., Tetrahedron, 1991, 47, 7911 to give Compound 78;
6) Compound 2 was modified by the procedure of Grehen, et al., Chem. Int. Ed. Eng., 1984, 23, 296 to give Compound 79;
7) Compound 2 was modified by the procedure of Tietze, et al., Liebigs Ann. Chem., 1988, 9-12 to give Compound 80;
8) Compound 2 was modified by the procedure of Abell, et al., Aust. J Chem., 1993, 46, 1473 to give Compound 82.

Numerous references are cited hereinabove, and the contents of all cited references are incorporated by reference herein.

What is claimed is:

1. A method of killing, or suppressing the growth of, an ecto- or endoparasite, wherein:

the method comprises contacting a susceptible ecto- or endoparasite with an effective amount of a 2-phenyl-3-(1H-pyrrol-2-yl)acrylonitrile compound of Formula 1:

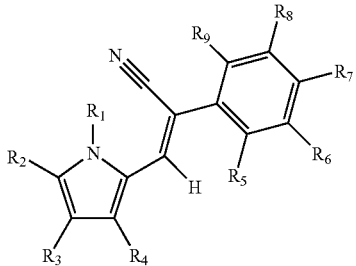

Formula 1 or a pharmaceutically acceptable salt thereof; wherein $R_1$ is selected from the group consisting of H, lower alkyl, and the following optionally substituted groups:

alkoxyalkyl, alkoxyalkoxyalkyl, 1,1-(dialkoxy)alkyl, 1-alkoxy-1-alkylmethyl, aroyl, alkanoyl, arylalkyl, alkyloxyalkanoyl, alkoxycarbonyl, arylalkoxycarbonyl, arylsulfonyl, alkylarylsulfonyl, alkylalkenyl, N-alkylcarbamoyl, N,N-dialkylcarbamoyl, N-alkylthiocarbamoyl, and N,N-dialkylthiocarbamoyl; and $R_2$-$R_9$ are independently selected from the group consisting of H, nitro, cyano, halo, and the following optionally substituted groups:

alkyl, aryl, cycloalkyl, cycloalkenyl, alkylcycloalkyl, alkylcycloalkenyl, cycloalkylalkyl, arylalkyl, aryloxyalkyl, arylthioalkyl, haloalkyl, haloalkenyl, haloalkynyl, haloaryl, halocycloalkyl, alkoxy, alkenyloxy, alkynyloxy, aryloxy, cycloalkyloxy, cycloalkenyloxy, alkylcycloalkyloxy, alkylcycloalkenyloxy, cycloalkylalkyloxy, arylalkoxy, aryloxyalkoxy, arylthioalkyloxy, haloalkoxy, haloalkenyloxy, haloalkynyloxy, haloaryloxy, and halocycloalkoxy, except that $R_5$ and $R_6$ or $R_6$ and $R_7$ may alternatively together form, in combination with the atoms to which they are attached, an optionally substituted 5- to 7-member.

2. The method of claim 1, wherein $R_5$ and $R_6$ or $R_6$ and $R_7$ together form, in combination with the atoms to which they are attached, a 5- to 7-member ring.

3. The method of claim 1, wherein $R_1$ is selected from the group consisting of $(CH_3CH_2O)_2CH$— and $CH_3CH_2OCH(CH_3)$—.

4. A method of killing, or suppressing the growth of, an ecto- or endoparasite, wherein:

the method comprises contacting a susceptible ecto- or endoparasite with an effective amount of a 2-phenyl-3-(1H-pyrrol-2-yl)acrylonitrile compound of Formula 1:

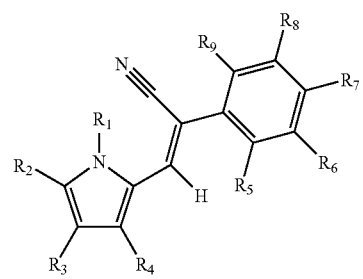

Formula 1 or a pharmaceutically acceptable salt thereof; wherein $R_1$ is selected from the group consisting of H and the following optionally substituted groups:

lower alkyl, alkoxyalkyl, alkoxyalkoxyalkyl, 1,1-(dialkoxy)alkyl, 1-alkoxy-1-alkylmethyl, aroyl, alkanoyl, arylalkyl, alkoxycarbonyl, arylalkoxycarbonyl, arylsulfonyl, alkylarylsulfonyl, alkylalkenyl, N-alkylcarbamoyl, N,N-dialkylcarbamoyl, N-alkylthiocarbamoyl and N,N-dialkylthiocarbamoyl; and $R_2$-$R_9$ are independently selected from the group consisting of H, nitro, cyano, halo, and the following optionally substituted groups:

alkyl, alkenyl, alkynyl, aryl, cycloalkyl, haloalkyl, haloalkenyl, haloalkynyl, haloaryl, halocycloalkyl, alkoxy, alkenyloxy, aryloxy, cycloalkyloxy, arylalkoxy, aryloxyalkoxy, haloalkoxy, haloalkenyloxy, haloaryloxy, alkylthio, arylthio, cycloalkylthio, arylalkylthio, and aryloxyalkylthio.

5. A method of killing, or suppressing the growth of, an ecto- or endoparasite, wherein:

the method comprises contacting a susceptible ecto- or endoparasite with an effective amount of a 2-phenyl-3-(1H-pyrrol-2-yl)acrylonitrile compound of Formula 1:

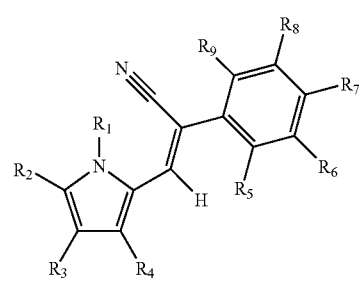

Formula 1 or a pharmaceutically acceptable salt thereof; wherein $R_2$-$R_4$ are independently selected from the group consisting of H, halo, optionally substituted alkyl, and optionally substituted alkoxy; and $R_5$-$R_9$ are independently selected from the group consisting of H, nitro, cyano, halo, and the following optionally substituted groups:

alkyl, alkenyl, alkynyl, aryl, cycloalkyl, haloalkyl, haloaryl, halocycloalkyl, alkoxy, alkenyloxy, aryloxy, cycloalkyloxy, arylalkoxy, haloalkoxy, and haloaryloxy, except that $R_5$ and $R_6$ or $R_6$ and $R_7$ may alternatively together form, in combination to the atoms to which they are attached, a 5- to 7-member ring.

6. The method of claim 1, wherein:
$R_1$ is selected from the group consisting of H, $CH_3$, ethoxymethyl, diethoxymethyl, propanoyl, benzyl, $CH_3CH_2NC(O)$, tert-butoxycarbonyl, 2-methyl prop-1-enyl, benzoyl, tosyl, $(CH_3)_2NC(S)$, $CH_3OC(O)$, and benzyloxycarbonyl;
$R_2$ is selected from the group consisting of H and Cl;
$R_3$ is selected from the group consisting of H, Cl, and Br;
$R_4$ is H;
$R_5$ is selected from the group consisting of H, Cl, Br $CH_3$, cyano, $CF_3$, phenyl, and methoxy;
$R_6$ is selected from the group consisting of H, Cl, F, Br, $CF_3$, phenyloxy, and $CH_3$;
$R_7$ is selected from the group consisting of H, Cl, F, $CH_3$, methoxy, t-butyl, phenyl, and cyano; and
$R_8$ and $R_9$ are independently selected from the group consisting of H, halo, and $CF_3$.

7. The method of claim 1, wherein:
$R_1$ is selected from the group consisting of H, $CH_3$, ethoxymethyl, diethoxymethyl, propanoyl, benzyl, $CH_3CH_2NC(O)$, tert-butoxycarbonyl, 2-methyl prop-1-enyl, benzoyl, tosyl, $(CH_3)_2NC(S)$, $CH_3OC(O)$ and benzyloxycarbonyl;
$R_2$ is selected from the group consisting of H and Cl;
$R_3$ is selected from the group consisting of H, Cl, and Br;
$R_4$ is H;
as to $R_5$, $R_6$, and $R_7$:
one of $R_5$ and $R_7$ is an independent substituent such that:
$R_5$ is selected from the group consisting of H, Cl, Br $CH_3$, cyano, $CF_3$, phenyl and methoxy, or
$R_7$ is selected from the group consisting of H, Cl, F, $CH_3$, methoxy, t-butyl, phenyl, and cyano; and
$R_6$ and the other of $R_5$ and $R_7$ together form, in combination with the atoms to which they are attached, phenyl; and
$R_8$ and $R_9$ are independently selected from the group consisting of H, halo, and $CF_3$.

8. The method of claim 1, wherein the method comprises contacting a susceptible ecto- or endoparasite with an effective amount of a 2-phenyl-3-(1H-pyrrol-2-yl)acrylonitrile compound of Formula 1 selected from the group identified in the following Tables or a pharmaceutically acceptable salt thereof:

TABLE 1a

| No | $R_1$ | $R_3$ | $R_2$ | $R_5$ | $R_6$ | $R_7$ | $R_8$ | $R_9$ |
|---|---|---|---|---|---|---|---|---|
| 1 | H | H | H | H | Cl | H | H | H |
| 2 | H | H | H | H | H | Cl | H | H |
| 3 | H | Cl | Cl | H | H | Cl | H | H |
| 4 | H | H | H | H | H | $CF_3$ | H | H |
| 5 | $CH_3$ | H | H | H | Cl | H | H | H |
| 6 | $CH_3$ | H | H | H | H | Cl | H | H |
| 7 | EOM | H | H | H | H | Cl | H | H |
| 8 | EOM | H | H | H | H | $CF_3$ | H | H |
| 9 | H | H | H | H | $CF_3$ | H | H | H |
| 10 | H | H | H | H | F | H | H | H |
| 11 | H | Br | H | H | H | $CF_3$ | H | H |
| 12 | H | Br | H | H | $CF_3$ | H | H | H |
| 13 | H | H | H | Cl | H | Cl | H | H |
| 14 | H | H | H | H | H | OMe | H | H |
| 15 | H | H | H | H | H | t-butyl | H | H |
| 16 | H | H | H | $CH_3$ | H | H | H | H |
| 17 | H | H | H | H | H | H | H | H |
| 18 | H | H | H | H | H | phenyl | H | H |
| 19 | H | H | H | H | H | cyano | H | H |
| 20 | H | H | H | H | H | cyano | H | H |
| 21 | $CH_3$ | H | H | H | H | $CF_3$ | H | H |
| 22 | $CH_3$ | H | H | H | $CF_3$ | H | H | H |
| 23 | H | Br | H | H | H | Cl | H | H |
| 24 | H | H | H | Cl | H | H | H | H |
| 25 | H | H | H | F | H | H | H | H |
| 26 | H | H | H | H | H | $CH_3$ | H | H |
| 27 | H | H | H | H | Cl | Cl | H | H |
| 28 | H | H | H | H | H | F | H | H |
| 29 | H | Br | H | H | Cl | Cl | H | H |
| 30 | H | Br | H | H | H | F | H | H |
| 31 | H | Br | H | H | F | H | H | H |
| 33 | H | H | H | H | H | Br | H | H |
| 35 | H | H | H | H | H | H | H | H |
| 36 | H | H | H | H | H | I | H | H |
| 37 | H | H | H | cyano | H | H | H | H |
| 38 | H | H | H | Br | H | H | H | H |
| 39 | H | H | H | H | Br | H | H | H |
| 40 | H | H | H | H | H | $NO_2$ | H | H |
| 41 | DOM | H | H | H | H | Cl | H | H |
| 42 | DOM | H | H | H | H | cyano | H | H |
| 43 | DOM | H | H | H | H | H | H | F |
| 44 | DOM | H | H | H | H | $NO_2$ | H | H |
| 45 | DOM | H | H | H | Cl | H | H | H |
| 46 | DOM | H | H | H | F | H | H | H |
| 47 | H | H | H | H | F | F | H | H |
| 48 | H | H | H | F | H | Cl | H | H |
| 49 | EOM | H | H | H | H | F | H | H |
| 50 | EOM | H | H | cyano | H | H | H | H |
| 51 | EOM | H | H | H | H | Br | H | H |
| 52 | EOM | H | H | Cl | H | H | H | Cl |
| 54 | EOM | H | H | Cl | H | H | H | H |
| 55 | EOM | H | H | F | H | H | H | H |
| 56 | EOM | H | H | H | Cl | Cl | H | H |
| 57 | EOM | H | H | $CF_3$ | H | H | H | H |
| 58 | EOM | H | H | H | Br | H | H | H |
| 59 | EOM | H | H | H | $CF_3$ | H | $CF_3$ | H |
| 60 | EOM | H | H | F | H | F | H | H |
| 61 | EOM | H | H | F | H | H | H | F |
| 62 | EOM | H | H | F | H | H | H | H |
| 63 | EOM | H | H | H | $CH_3$ | H | H | H |
| 64 | EOM | H | H | H | H | $CH_3$ | H | H |
| 67 | H | H | H | Cl | H | H | H | F |
| 68 | H | H | H | H | $CF_3$ | H | $CF_3$ | H |
| 69 | H | H | H | F | H | F | H | H |
| 70 | H | H | H | F | H | H | H | F |
| 71 | H | H | H | H | OPh | H | H | H |
| 72 | H | H | H | H | $CH_3$ | H | H | H |
| 73 | H | H | H | Br | F | H | H | H |
| 74 | H | H | H | Cl | H | F | H | H |
| 75 | H | H | H | H | H | ethyl | H | H |
| 76 | propanoyl | H | H | H | H | Cl | H | H |
| 77 | benzyl | H | H | H | H | Cl | H | H |
| 78 | $Et_2NC(O)$ | H | H | H | H | Cl | H | H |
| 79 | Boc | H | H | H | H | Cl | H | H |
| 80 | 3-M-2-B | H | H | H | H | Cl | H | H |
| 81 | H | H | H | H | Cl | F | H | H |
| 82 | benzoyl | H | H | H | H | Cl | H | H |
| 83 | tosyl | H | H | H | H | Cl | H | H |
| 84 | $Me_2NC(S)$ | H | H | H | H | Cl | H | H |
| 85 | MeOC(O) | H | H | H | H | Cl | H | H |
| 86 | Cbz | H | H | H | H | Cl | H | H |
| 87 | H | H | H | H | H | i-propyl | H | H |
| 88 | H | H | H | $CH_3$ | H | $CH_3$ | H | H |
| 89 | H | H | H | Ph | H | H | H | H |
| 90 | H | H | H | $CF_3$ | H | H | H | H |
| 91 | H | H | H | OMe | H | H | H | H | wherein:
"No" = Compound number;
"EOM" = ethoxymethyl;
"DOM" = diethoxymethyl;
"Boc" = tert-butoxycarbonyl;
"Cbz" = benzyloxycarbonyl;
"Et" = ethyl;
"Me" = methyl;
"Ph" = phenyl;
"OMe" = methoxy;
"3-M-2-B" = 3-methyl-2-butenyl;
"i-propyl" = isopropyl; and
$R_4$ is H; and

TABLE 1b

| Compound No. | Name and Structure |
|---|---|
| 19 | 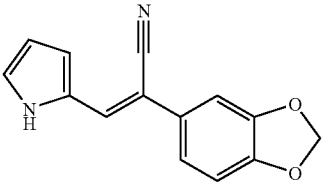<br>2-(3,4-methylenedioxy)phenyl-3-(1H-pyrrol-2-yl)acrylonitrile |
| 32 | 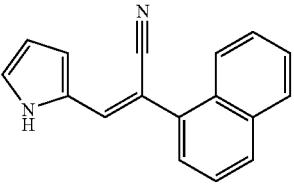<br>2-(1-naphthyl)-3-(1H-pyrrol-2-yl)acrylonitrile |
| 34 | 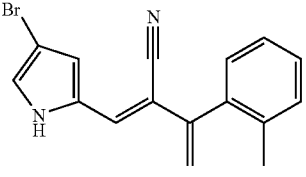<br>2-(1-naphthyl)-3-(4-bromo-1H-pyrrol-2-yl)acrylonitrile |
| 53 | 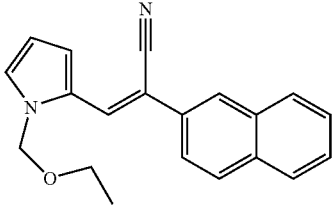<br>2-(2-naphthyl)-3-(1-ethoxymethyl-1H-pyrrol-2-yl)acrylonitrile |
| 65 | 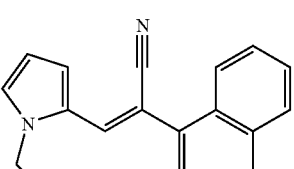<br>2-(1-naphthyl)-3-(1-ethoxymethyl-1H-pyrrol-2-yl)acrylonitrile |

TABLE 1b-continued

| Compound No. | Name and Structure |
|---|---|
| 66 | 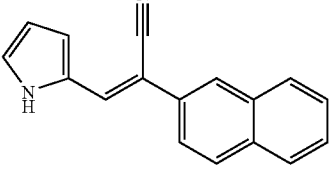<br>2-(2-naphthyl)-3-(1H-pyrrol-2-yl)acrylonitrile. |

9. The method of claim 1 wherein the parasite to be killed or suppressed is an ectoparasite.

10. The method of claim 1 wherein the parasite to be killed or suppressed is an endoparasite.

11. The method of claim 1 wherein the parasite to be killed or suppressed is infecting or infesting an animal, in vivo or ex vivo.

12. The method of claim 1 wherein the parasite to be killed or suppressed is infecting or infesting a plant, in vivo or ex vivo.

13. The method of claim 1 wherein the parasite to be killed or suppressed is present on an inanimate object or surface.

14. The method of claim 1 wherein the parasite to be killed or suppressed is located in vivo in an animal.

15. The method of claim 14, a wherein the contacting of the ecto- or endoparasite is conducted by administering an effective amount of the 2-phenyl-3-(1H-pyrrol-2-yl)acrylonitrile compound of Formula 1 or pharmaceutically acceptable salt thereof to the animal.

16. The method of claim 6 wherein the parasite to be killed or suppressed is located in vivo in an animal.

17. The method of claim 16, wherein the contacting of the ecto- or endoparasite is conducted by administering an effective amount of the 2-phenyl-3-(1H-pyrrol-2-yl)acrylonitrile compound of Formula 1 or pharmaceutically acceptable salt thereof to the animal.

18. The method of claim 4 wherein the parasite to be killed or suppressed is located in vivo in an animal.

19. The method of claim 18, wherein the contacting of the ecto- or endoparasite is conducted by administering an effective amount of the 2-phenyl-3-(1H-pyrrol-2-yl)acrylonitrile compound of Formula 1 or pharmaceutically acceptable salt thereof to the animal.

20. The method of claim 5 wherein the parasite to be killed or suppressed is located in vivo in an animal.

21. The method of claim 20, wherein the contacting of the ecto- or endoparasite is conducted by administering an effective amount of the 2-phenyl-3-(1H-pyrrol-2-yl)acrylonitrile compound of Formula 1 or pharmaceutically acceptable salt thereof to the animal.

22. The method of claim 7, wherein the parasite to be killed or suppressed is located in vivo in an animal.

23. The method of claim 22, wherein the contacting of the ecto- or endoparasite is conducted by administering an effective amount of the 2-phenyl-3-(1H-pyrrol-2-yl)acrylonitrile compound of Formula 1 or pharmaceutically acceptable salt thereof to the animal.

\* \* \* \* \*